US012692398B2

(12) United States Patent　　(10) Patent No.:　US 12,692,398 B2

Yin et al.　　(45) Date of Patent:　Jul. 28, 2026

(54) MAGNETICALLY TUNABLE PLASMON COUPLING OF NANOSHELLS ENABLED BY SPACE-FREE CONFINED GROWTH

(71) Applicant: THE REGENTS OF THE UNIVERSITY OF CALIFORNIA, Oakland, CA (US)

(72) Inventors: Yadong Yin, Riverside, CA (US); Zhiwei Li, Riverside, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 537 days.

(21) Appl. No.: 18/247,960

(22) PCT Filed: Oct. 11, 2021

(86) PCT No.: PCT/US2021/054386

§ 371 (c)(1),
(2) Date: Apr. 5, 2023

(87) PCT Pub. No.: WO2022/076935

PCT Pub. Date: Apr. 14, 2022

(65) Prior Publication Data

US 2023/0383124 A1　　Nov. 30, 2023

Related U.S. Application Data

(60) Provisional application No. 63/089,765, filed on Oct. 9, 2020.

(51) Int. Cl.
*C09C 3/10*　　(2006.01)
*B22F 1/103*　　(2022.01)
(Continued)

(52) U.S. Cl.
CPC .............. *C09C 3/006* (2013.01); *B22F 1/103* (2022.01); *B22F 1/18* (2022.01); *C08K 9/10* (2013.01);
(Continued)

(58) Field of Classification Search
CPC ........... C09C 3/006; C09C 1/24; C09C 3/066; C09C 3/10; B22F 1/103; B22F 1/18;
(Continued)

(56) References Cited

U.S. PATENT DOCUMENTS 7,829,140 B1 * 11/2010 Zhong ....................... C09C 1/24
427/212
8,343,627 B2 * 1/2013 Zhong .............. G01N 33/54326
428/403
(Continued)

FOREIGN PATENT DOCUMENTS

AU　　　2016201510 A1　　9/2017
CN　　　　1747078 A　　3/2006
(Continued)

OTHER PUBLICATIONS

Office Action/Search Report (First Office Action) issued on Jun. 26, 2025, in corresponding Chinese Patent Application No. 202180083301.3 and English translation of the Office Action/Search Report. (24 pages).

(Continued)

*Primary Examiner* — Cam N. Nguyen

(74) *Attorney, Agent, or Firm* — Buchanan Ingersoll & Rooney PC

(57)　　　　　ABSTRACT

A method of forming magnetic/plasmonic hybrid structures is disclosed. The method includes synthesizing colloidal magnetic nanoparticles; modifying the magnetic nanoparticles in a solution of a polymeric ligand; binding metal seed nanoparticles to the surface of the magnetic nanoparticles;
(Continued)

and performing a seed-mediated growth on the metal seed nanoparticles by reducing a metal salt in solution to form the magnetic/plasmonic hybrid structures.

11 Claims, 18 Drawing Sheets

(51) Int. Cl.

| | |
|---|---|
| B22F 1/18 | (2022.01) |
| B82Y 5/00 | (2011.01) |
| B82Y 15/00 | (2011.01) |
| B82Y 20/00 | (2011.01) |
| B82Y 25/00 | (2011.01) |
| B82Y 40/00 | (2011.01) |
| C08K 9/10 | (2006.01) |
| C09C 1/24 | (2006.01) |
| C09C 3/00 | (2006.01) |
| C09C 3/06 | (2006.01) |
| G01N 21/31 | (2006.01) |
| H01F 1/01 | (2006.01) |

(52) U.S. Cl.
CPC .............. *C09C 1/24* (2013.01); *C09C 3/066* (2013.01); *C09C 3/10* (2013.01); *G01N 21/31* (2013.01); *H01F 1/01* (2013.01); *B22F 2301/255* (2013.01); *B22F 2302/25* (2013.01); *B22F 2303/20* (2013.01); *B22F 2998/10* (2013.01); *B82Y 5/00* (2013.01); *B82Y 15/00* (2013.01); *B82Y 25/00* (2013.01); *B82Y 40/00* (2013.01); *C01P 2004/04* (2013.01); *C01P 2004/34* (2013.01); *C01P 2004/64* (2013.01); *C01P 2006/42* (2013.01); *C08K 2201/01* (2013.01); *C08K 2201/011* (2013.01)

(58) Field of Classification Search
CPC ............ B22F 2301/255; B22F 2302/25; B22F 2303/20; B22F 2998/10; C08K 9/10; C08K 2201/01; C08K 2201/011; G01N 21/31; H01F 1/01; H01F 1/0054; B82Y 5/00; B82Y 15/00; B82Y 25/00; B82Y 40/00; B82Y 20/00; C01P 2004/04; C01P 2004/34; C01P 2004/64; C01P 2006/42; G02B 5/008
USPC ........................................................ 423/632
See application file for complete search history.

(56) References Cited

U.S. PATENT DOCUMENTS

| | | | | |
|---|---|---|---|---|
| 8,383,085 | B2 * | 2/2013 | Hegmann | .............. B82Y 30/00 424/646 |
| 8,802,234 | B2 | 8/2014 | Che et al. | |
| 9,327,314 | B2 * | 5/2016 | Zhong | ...................... B01J 13/02 |
| 9,801,962 | B2 * | 10/2017 | Sun | ........................... B01J 13/02 |
| 9,952,209 | B2 | 4/2018 | Huang et al. | |
| 10,006,908 | B2 * | 6/2018 | Zhong | ...................... B05D 7/00 |
| 10,113,924 | B2 | 10/2018 | Yin et al. | |
| 10,191,042 | B2 * | 1/2019 | Zhong | ................... G01N 33/553 |
| 10,561,745 | B2 | 2/2020 | Tomitaka et al. | |
| 10,662,066 | B2 * | 5/2020 | Guo | ........................ C01B 33/18 |
| 11,161,747 | B2 * | 11/2021 | Guo | ........................ B82Y 20/00 |
| 11,680,113 | B2 * | 6/2023 | Lundberg | ................. C08J 9/286 525/218 |
| 2012/0168669 | A1 | 7/2012 | Che et al. | |
| 2015/0037818 | A1 | 2/2015 | Huang et al. | |
| 2018/0114637 | A1 | 4/2018 | Yin et al. | |
| 2020/0308422 | A1 | 10/2020 | Watanabe et al. | |
| 2021/0276084 | A1 * | 9/2021 | Yi | .......................... C01G 49/06 |

FOREIGN PATENT DOCUMENTS

| | | |
|---|---|---|
| CN | 101280092 A | 10/2008 |
| CN | 107710350 A | 2/2018 |
| CN | 110243801 A | 9/2019 |
| CN | 111069622 A | 4/2020 |
| WO | 2016/150406 A1 | 9/2016 |

OTHER PUBLICATIONS

Extended European Search Report issued on Oct. 15, 2024, in corresponding European Patent Application No. 21878690.3. (10 pages).

Khan et al., "Characterisation and Manipulation of Polarisation Response in Plasmonic and Magneto-Plasmonic Nanostructures and Metamaterials", Symmetry, vol. 12, No. 8, (Aug. 17, 2020), XP055902864. (57 pages).

Lai et al., "A review of the preparation and application of magnetic nanoparticles for surface-enhanced Raman scattering", Journal of Material Science, vol. 53, No. 12, (Feb. 6, 2018), pp. 8677-8698, XP036467606.

Lin et al., "Yolk-Shell Nanostructures: Design, Synthesis, and Biomedical Applications", Advanced Materials, vol. 30, No. 6, (Dec. 27, 2017), XP071873970. (30 pages).

International Search Report (PCT/ISA/210) and Written Opinion (PCT/ISA/237) mailed on Jan. 27, 2022, by the U.S. Patent Office as the International Searching Authority for International Application No. PCT/US2021/054386. (16 pages).

Besteiro, et al., "Plasmonic Glasses and Films Based on Alternative Inexpensive Materials for Blocking Infrared Radiation", Nano Letters, vol. 18, No. 5, 2018, pp. 3147-3156.

Brinson, et al., "Nanoshells Made Easy: Improving Au Layer Growth on Nanoparticle Surfaces", Langmuir, vol. 24, No. 24, Dec. 16, 2008, pp. 14166-14171.

Byers, et al., "From Tunable Core-Shell Nanoparticles to Plasmonic Drawbridges: Active Control of Nanoparticle Optical Properties", Science Advances, vol. 1, No. 11, Article No. e1500988, Dec. 4, 2015, pp. 1-9 (10 pages).

Chen, et al., "Assembling Color on the Nanoscale: Multichromatic Switchable Pixels from Plasmonic Atoms and Molecules", Advanced Materials, vol. 28, No. 18, May 2016, pp. 3522-3527.

Feng, et al., "Self-Aligned Anisotropic Plasmonic Nanostructures", Advanced Materials, vol. 31, No. 19, Article No. 1900789, May 2019, pp. 1-8.

Gao, et al., "One-Step Seeded Growth of Au Nanoparticles with Widely Tunable Sizes", Nanoscale, vol. 4, 2012, pp. 2875-2878.

Gao, et al., "Seeded Growth Route to Noble Metal Nanostructures", Journal of Materials Chemistry C, vol. 1, 2013, pp. 3898-3909.

Ge, et al., "Highly Tunable Superparamagnetic Colloidal Photonic Crystals", Angewandte Chemie International Edition, vol. 46, No. 39, 2007, pp. 7428-7431.

Ge, et al., "Responsive Photonic Crystals", Angewandte Chemie International Edition, vol. 50, No. 7, Feb. 11, 2011, pp. 1492-1522.

Ge, et al., "Superparamagnetic Magnetite Colloidal Nanocrystal Clusters", Angewandte Chemie International Edition, vol. 46, No. 23, Jun. 4, 2007, pp. 4342-4345.

Hisu, et al., "Transparent Displays Enabled by Resonant Nanoparticle Scattering", Nature Communications, vol. 5, Article No. 3152, 2014, pp. 1-6.

Jain, et al., "On the Universal Scaling Behavior of the Distance Decay of Plasmon Coupling in Metal Nanoparticle Pairs: A Plasmon Ruler Equation", Nano Letters., vol. 7, No. 7, 2007, pp. 2080-2088.

Jain, et al., "Universal Scaling of Plasmon Coupling in Metal Nanostructures: Extension from Particle Pairs to Nanoshells", Nano Letters, vol. 7, No. 9, Sep. 2007, pp. 2854-2858.

Jiang, et al., "(Gold Nanorod Core)/(Polyaniline Shell) Plasmonic Switches with Large Plasmon Shifts and Modulation Depths", Advanced Materials, vol. 26, No. 20, May 28, 2014, pp. 3282-3289.

Kim, et al., "Designed Fabrication of Multifunctional Magnetic Gold Nanoshells and Their Application to Magnetic Resonance Imaging and Photothermal Therapy", Angewandte Chemie International Edition, vol. 118, No. 46, Nov. 27, 2006, pp. 7918-7922.

(56) References Cited

OTHER PUBLICATIONS

Kim, et al., "Structural Colour Printing Using a Magnetically Tunable and Lithographically Fixable Photonic Crystal", Nature Photonics, vol. 3, Sep. 2009, pp. 534-540.

Lal, et al., "Nano-Optics from Sensing to Waveguiding", Nature Photonics, vol. 1, 2007, pp. 641-648.

Levin, et al., "Magnetic-Plasmonic Core-Shell Nanoparticles", ACS Nano, vol. 3, No. 6, Jun. 23, 2009, pp. 1379-1388.

Li, et al., "Colloidal Assembly and Active Tuning of Coupled Plasmonic Nanospheres", Trends in Chemistry, vol. 2, No. 7, Jul. 2020, pp. 593-608.

Li, et al., "Coupling Magnetic and Plasmonic Anisotropy in Hybrid Nanorods for Mechanochromic Responses", Nature Communications, vol. 11, Article No. 2883, 2020, pp. 1-11.

Li, et al., "Magnetic Assembly of Nanocubes for Orientation-Dependent Photonic Responses", Nano Letters, vol. 19, No. 9, 2019, pp. 6673-6680.

Li, et al., "Magnetic Targeting Enhanced Theranostic Strategy Based on Multimodal Imaging for Selective Ablation of Cancer", Advanced Functional Materials, vol. 24, No. 16, Apr. 23, 2014, pp. 2312-2321 (11 pages).

Li, et al., "Smart Materials by Nanoscale Magnetic Assembly", Advanced Functional Materials, vol. 30, Article No. 1903467, Jan. 10, 2020, pp. 1-17 (18 pages).

Li, et al., "Stimuli-Responsive Optical Nanomaterials", Advanced Materials, vol. 31, No. 15, Article No. 1807061, Apr. 2019, pp. 1-33.

Lin , et al., "One-Dimensional Plasmon Coupling by Facile Self-Assembly of Gold Nanoparticles into Branched Chain Networks", Advanced Materials; vol. 17, No. 21, Nov. 2005, pp. 2553-2559.

Liu, et al., "Dynamic Color-Switching of Plasmonic Nanoparticle Films", Angewandte Chemie International Edition, vol. 58, No. 45, Nov. 4, 2019, pp. 16307-16313.

Liu, et al., "Extension of The Stober Method to the Preparation of Monodisperse Resorcinol-Formaldehyde Resin Polymer and Carbon Spheres", Angewandte Chemie, vol. 123, No. 26, Jun. 20, 2011, pp. 6069-6073.

Liu, et al., "Reversible Assembly and Dynamic Plasmonic Tuning of Ag Nanoparticles Enabled by Limited Ligand Protection", Nano Letters, vol. 18, No. 8, Aug. 8, 2018, pp. 5312-5318.

Liu, et al., "Size-Tailored Synthesis of Silver Quasi-Nanospheres by Kinetically Controlled Seeded Growth", Langmuir, vol. 29, No. 33, Aug. 20, 2013, pp. 10559-10565.

Montelongo, et al., "Plasmonic Nanoparticle Scattering for Color Holograms", Proceedings of the National Academy of Sciences, vol. 111, No. 35, Sep. 2, 2014, pp. 12679-12683.

Pang, et al., "1D Nanocrystals With Precisely Controlled Dimensions, Compositions, and Architectures", Science, vol. 353, No. 6305, Sep. 16, 2016, pp. 1268-1272 (6 pages).

Peng, et al., "Scalable Electrochromic Nanopixels Using Plasmonics", Science Advances, vol. 5, No. 5, Article No. eaaw2205, May 2019, pp. 1-8 (9 pages).

Prodan, et al., "A Hybridization Model for the Plasmon Response of Complex Nanostructures", Science, vol. 302, No. 5644, Oct. 17, 2003, pp. 419-422 (5 pages).

Radloff, et al., "Plasmonic Properties of Concentric Nanoshells", Nano Letters, vol. 4, No. 7, 2004, pp. 1323-1327.

Shen, et al., "Multifunctional Fe3O4@Ag/SiO2/Au Core-Shell Microspheres as a Novel SERS-Activity Label via Long-Range Plasmon Coupling", Langmuir, vol. 29, No. 2, Jan. 15, 2013, pp. 690-695.

Sonnichsen, et al., "A Molecular Ruler Based on Plasmon Coupling of Single Gold and Silver Nanoparticles", Nature Biotechnology, vol. 23, No. 6, Jun. 2005, pp. 741-745.

Wang, et al., "Anisotropically Shaped Magnetic/Plasmonic Nanocomposites for Information Encryption and Magnetic-Field-Direction Sensing", Research, vol. 2018, Article No. 7527825, 2018, 13 pages.

Wang, et al., "Magnetic Tuning of Plasmonic Excitation of Gold Nanorods", Journal of the American Chemical Society, vol. 135, No. 41, Oct. 16, 2013, pp. 15302-15305.

Wang, et al., "Plasmonic Nanostructures: Artificial Molecules", Accounts of Chemical Research, vol. 40, No. 1, Jan. 2007, pp. 53-62.

Weiss, Joseph, "The Catalytic Decomposition of HydroGen Peroxide on Different Metals", Transactions of the Faraday Society, vol. 31, 1935, pp. 1547-1557.

Xu, et al., "Colloidal Assembly Approaches to Micro/ Nanostructures of Complex Morphologies", Small, vol. 14, No. 35, Article No. 1801083, Aug. 2018, pp. 1-27.

Yang, et al., "Precisely Size-Tunable Magnetic/Plasmonic Core/ Shell Nanoparticles with Controlled Optical Properties", Angewandte Chemie International Edition, vol. 127, Oct. 5, 2015, pp. 12259-12264.

Yu, et al., "Thermal Synthesis of Silver Nanoplates Revisited: A Modified Photochemical Process", ACS Nano, vol. 8, No. 10, Oct. 28, 2014, pp. 10252-10261.

Zhang, et al., "A Systematic Study of the Synthesis of Silver Nanoplates: Is Citrate a "Magic" Reagent?", Journal of the American Chemical Society, vol. 133, No. 46, Nov. 23, 2011, pp. 18931-18939.

Zhang, et al., "Tailored Synthesis of Superparamagnetic Gold Nanoshells with Tunable Optical Properties", Advanced Materials, vol. 22, No. 17, May 4, 2010, pp. 1905-1909.

Zhou, et al., "Formation of Resorcinol-Formaldehyde Hollow Nanoshells Through a Dissolution-Regrowth Process", Nanoscale, vol. 12, 2020, pp. 15460-15465.

Request for the Submission of an Opinion dated Jan. 26, 2026, issued in corresponding Korean Patent Application No. 10-2023-7015123, with English translation thereof. (12 pages).

Notification to Grant Patent Right for Invention dated Nov. 13, 2025, issued in the corresponding Chinese Patent Application No. 202180083301.3, 6 pages including 2 pages of English Translation.

* cited by examiner

MAGNETICALLY TUNABLE PLASMON COUPLING OF NANOSHELLS ENABLED BY SPACE-FREE CONFINED GROWTH

CROSS REFERENCE TO RELATED APPLICATIONS

This application is a U.S. National Stage Application filed under 35 U.S.C. 371 (a) of International Patent Application No. PCT/US2021/054386 filed on Oct. 11, 2021, which claims the benefit of U.S. Provisional Application No. 63/089,765, filed Oct. 9, 2020, which are incorporated by reference in their entirety.

GOVERNMENT LICENSE RIGHTS

This invention was made with government support under CHE-1808788 awarded by the National Science Foundation. The government has certain rights in the invention.

TECHNICAL FIELD

The present disclosure generally relates to magnetically tunable plasmon coupling of nanoshells enabled by space-free confined growth, and more particularly, for example, to a method of forming magnetic/plasmonic hybrid structures.

BACKGROUND

Resonant scattering of plasmonic nanoparticles has attracted increasing attention due to its emerging applications in flexible transparent displays, optical metasurfaces, smart windows, wearable electronics, and color holograms. These applications rely on the strong localized surface plasmon resonance (LSPR) that can efficiently scatter light of a particular wavelength while being "transparent" at off-resonance wavelengths. Considerable research efforts have been made to exploit plasmonic structures with large scattering cross-sections and tunable resonant wavelengths by controlling their sizes, morphologies, and chemical surroundings. It has been recognized in earlier studies that large plasmonic nanospheres, particularly of Au and Ag, have scattering-dominant LSPR, whose resonant wavelength can be tuned from visible to near-infrared (NIR) regions by simply increasing the particle size. Since LSPR weakens along the depth from the surface, the scattering efficiency decreases significantly as the particle size increases. For Au nanoparticles, its active skin depth was estimated to be only tens of nanometers, leading to relatively low scattering efficiency in large solid particles due to the higher percentage of inactive inner atoms.

Plasmonic nanoshells, with noble metal coatings on dielectric cores, exhibit much higher scattering efficiency and wavelength tunability in LSPR than their solid counterparts. However, their practical implementation has been challenged by the lack of robust methods for large-scale production of high-quality nanoshells with tunable resonant scattering and considerably low off-resonance absorption. A conventional approach to Au nanoshells is to grow them directly from the seeds pre-immobilized on the organic or inorganic cores. Careful control of the seed binding and growth kinetics can be required to avoid self-nucleation, making the process difficult to scale up. A more critical issue can be in the production of uniform and thin nanoshells, as the free growth of multiple seeds only produces thick Au shells by fusion of large grains, which leads to low plasmonic activities and significantly broadened extinction due to the presence of high-density grain boundaries. The growth becomes especially problematic when the core size is below approximately 100 nm because of the uneven distribution of metal seeds, for example, gold (Au) seeds and the increased difficulty in controlling the growth kinetics on a highly curved surface. This poses additional challenges on fully exploiting the potentials of Au nanoshells in particularly biomedical applications because small and thin shells permit efficient extravasation into tissues or tumors, and they allow more convenient positioning of LSPR in the most biomedical relevant visible and NIR regions.

SUMMARY

In consideration of the above issues, it would be desirable to a space-free confined growth process that allows the creation of high-quality, for example, gold (Au), silver (Ag), or copper (Cu) nanoshells on relatively small magnetic $Fe_3O_4$ cores (for example, 10 nm to 150 nm) with excellent plasmonic properties. In accordance with an exemplary embodiment, the resulting core-shell nanoparticles can be magnetically assembled into plasmonic chains, which can exhibit dynamically tunable coupled resonant scattering.

In accordance with an exemplary embodiment, a soft, deformable, and highly permeable polymer shell is employed to mediate and confine the seeded growth of metallic metals, for example, Au, Ag, or Cu. The deformable polymer shell limits the seeded growth to its interface with the magnetic core and enables the regulation of the Au, Ag, or Cu growth without the need for creating an additional limiting space or gap in the templated synthesis. While its high deformability affords space for the formation of complete metallic shells, the elastic polymer shell suppresses the deposition of metal (e.g., Au, Ag, or Cu) atoms and therefore limits their growth along the radial directions. Further, the high magnetic susceptibility of the cores enables the development of a new scheme to actively and reversibly tune the plasmon coupling and resonant scattering of Au, Ag, or Cu nanoshells via the magnetic assembly of the hybrid nanoparticles into plasmonic chains, making them promising materials for creating novel transparent displays and anti-counterfeiting devices.

In accordance with an aspect, a method of forming magnetic/plasmonic hybrid structures comprising: synthesizing colloidal magnetic nanoparticles; modifying the magnetic nanoparticles in a solution of a polymeric ligand; binding metal seed nanoparticles to the surface of the magnetic nanoparticles; and performing a seed-mediated growth on the metal seed nanoparticles by reducing a metal salt in solution to form the magnetic/plasmonic hybrid structures.

In accordance with another aspect, a method for using magnetic/plasmonic structures in an anti-counterfeiting device, the method comprising: fixing one-dimensional plasmonic chains with pre-designed orientations in a solid polymer using a magnetic field; subjecting the one-dimensional plasmonic chains to a polarized light from a first direction, which exhibits a first color spectrum; and subjecting the one-dimensional plasmonic chains to the polarized light from a second direction, which exhibits a second color spectrum, the first color spectrum being different from the second color spectrum.

In accordance with a further aspect, a magnetic/plasmonic hybrid structure comprising: a magnetic nanoparticle core; a deformable and permeable polymeric ligand shell; and seeds of a metal attached to the magnetic nanoparticle core, the seeds of the metal configured to have limited growth as a result of the deformable and permeable polymeric ligand shell on the magnetic core suppressing a deposition of metal atoms and limiting growth of the metal atoms along a radial direction.

BRIEF DESCRIPTION OF THE DRAWINGS

FIGS. 1a-1f, wherein FIG. 1a is a schematic illustration of the seed-mediated growth of Au nanoshells on iron oxide nanospheres. TEM images of $Fe_3O_4$ nanospheres (FIG. 1b), $Fe_3O_4$/Au@RF (FIG. 1c), and $Fe_3O_4$@Au@RF nanospheres (FIG. 1d). Evolution of plasmonic peaks during the seeded growth of Au nanoshells on 125-nm (FIG. 1e) and 20-nm (FIG. 1f) $Fe_3O_4$ nanospheres.

FIG. 2e is an illustration of the UV-Vis spectra of $Fe_3O_4$@Au@RF nanospheres with different core diameters. FIG. 2f are digital pictures of a colloidal dispersion of $Fe_3O_4$@Au@RF nanospheres with a core diameter of (i) 20 nm, (ii) 70 nm, (iii) 125 nm, and (iv) 150 nm.

FIG. 3a illustrates optical properties of Au nanoshells prepared by using 70-nm $Fe_3O_4$ nanospheres as cores. FIG. 3b is an illustration of the light incidence direction in the plasmonic excitation of Au nanoshells (70-nm core and 25-nm shell, left panel) and the color-coded surface of the far-field radiation pattern of the Au nanoshells excited by light of 710 nm (right panel). FIG. 3c illustrates the corresponding surface Poynting vector (surface arrows) and electric field distribution (color maps) of the Au nanoshells. FIG. 3d illustrates the fabrication of PVA/Au composite films for transparent displays. The inner diameter of the gold nanoshells is 70 nm. FIG. 3e is a photograph of a composite film under natural lighting. FIGS. 3f and 3g are photographs showing PVA/Au composite films containing hybrid nanoparticles with 70-nm (FIG. 3f) and 20-nm (FIG. 3g) $Fe_3O_4$ cores. The letters were created by the projector and then illuminated on the films, with white light on the top row and monochromic light at the bottom row. FIG. 3h is a photograph of a pure PVA film under the same light illumination. Scale bars: 1 cm.

FIG. 4a illustrates measured extinction spectra of plasmonic chains under different field strength. FIG. 4b illustrates measured extinction spectra of the plasmonic chains under different orientations. FIG. 4c are polarized optical macroscopic (POM) images of $Fe_3O_4$@Au@RF nanoparticles under different magnetic fields. White arrows indicate the magnetic field directions. The polarization of incident light is horizontal.

FIG. 5a is a schematic illustration of the lithography process for the fabrication of thin films with different chain orientations. FIG. 5b are normal and polarized optical microscopic images of boundary areas with horizontal (left regions) and vertical (right regions) plasmonic nanochains. White arrows indicate the polarization of incident light. The panel on the bottom right is under ordinary light excitation. FIG. 5c are digital pictures of a pattern under horizontal (top) and vertical polarization (bottom). FIG. 5d are digital images of a pattern under horizontal (top), vertical (middle), and 45° polarization (bottom). Scale bars: 10 μm (FIG. 5b); FIG. 5c and 500 μm (FIG. 5c and FIG. 5d).

FIGS. 6d and 6e are simulated atomic scattering cross sections of Au nanoshells (FIG. 6d) and solid Au nanoparticles (FIG. 6e) with different diameters. The Au nanoshells of 25 nm thickness were used for simulations. FIG. 6f is a simulated atomic absorption cross-sections of Au nanoshells. FIG. 6g is a merit figure of scattering of Au nanoshells. FIG. 6h is a near-field electric field distribution (right) and Poynting vectors (left) of Au nanoshells excited at the resonant wavelength as indicated.

(FIG. 8b) FIG. 8c illustrates Zeta potential of magnetic nanoparticles before and after PEI modification.

FIGS. 11a and 11b illustrate in FIG. 11a, a typical TEM and FIG. 11b, a high-magnification TEM images of $Fe_3O_4$@Au@RF nanospheres using 125-nm colloidal nanoparticles as cores. The selective areas for high-resolution images is indicated by the dashed box in FIG. 11a.

FIG. 13d illustrates the extinction spectra of $Fe_3O_4$@Au nanoparticles. FIG. 13e illustrates the simulated extinction spectra of $Fe_3O_4$@Au nanoparticles. UV-Vis spectra of as-synthesized Au nanoshells before and after etching away RF: FIG. 13f is a 20-nm core and FIG. 13g is a 70-nm core. Insets in FIG. 13g: solutions of $Fe_3O_4$@Au@RF and $Fe_3O_4$@Au with 70-nm core under bright and dark fields. Pictures highlighted by black and red frames show the solutions before and after etching away RF shells, respectively.

FIGS. 14b and 14c are photographs showing the projection images of PVA/Au composite films as transparent displays made of 20 nm (FIG. 14b) and 70 nm (FIG. 14c) $Fe_3O_4$ nanospheres as cores. Scale bars: 1 cm.

FIG. 16b is an illustration of the localized electric field distribution at a separation of 5 nm, 20 nm, and 40 nm. The excitation wavelength from left to right is 750, 710, and 690 nm, respectively. FIG. 16c is a simulated extinction spectra of the plasmonic chain under different orientations. The interparticle separation was set to be 30 nm. FIG. 16d is an illustration of the localized electric field distribution of plasmonic chains under orientations of 0°, 45°, and 90°.

DETAILED DESCRIPTION

Reference will now be made in detail to the present preferred embodiments of the disclosure, examples of which are illustrated in the accompanying drawings.

In accordance with an exemplary embodiment, the unconventional space-free confined growth of metal nanoshells, for example, Au, Ag, or Cu nanoshells with well-defined plasmonic properties and active tuning of their plasmon coupling by the nanoscale magnetic assembly is disclosed. The seeded growth of Au exclusively occurred at the hard-soft interfaces between the $Fe_3O_4$ core and phenolic resin without the need of creating a limiting space, which represents a general and elegant approach to various core-shell nanostructures. The deformability of permeable phenolic layers plays an essential role in regulating the interfacial growth of Au, Ag, or Cu nanoshells. While the polymer elasticity suppresses the radial deposition of the atoms, for example, Au, Ag, and Cu atoms, their high deformability can afford enough spaces for the formation of conformal metallic shells. The coupled magnetic-plasmonic properties allow active tuning of the plasmon coupling and the resonant scattering of Au, Ag, or Cu nanoshells by the magnetic assembly of the hybrid nanoparticles into plasmonic chains, whose potentials in applications can be used in designing transparent displays and anti-counterfeiting devices.

Figures 6A, 6B, 6C, 6D, 6E, 6F, 6G, 6H:
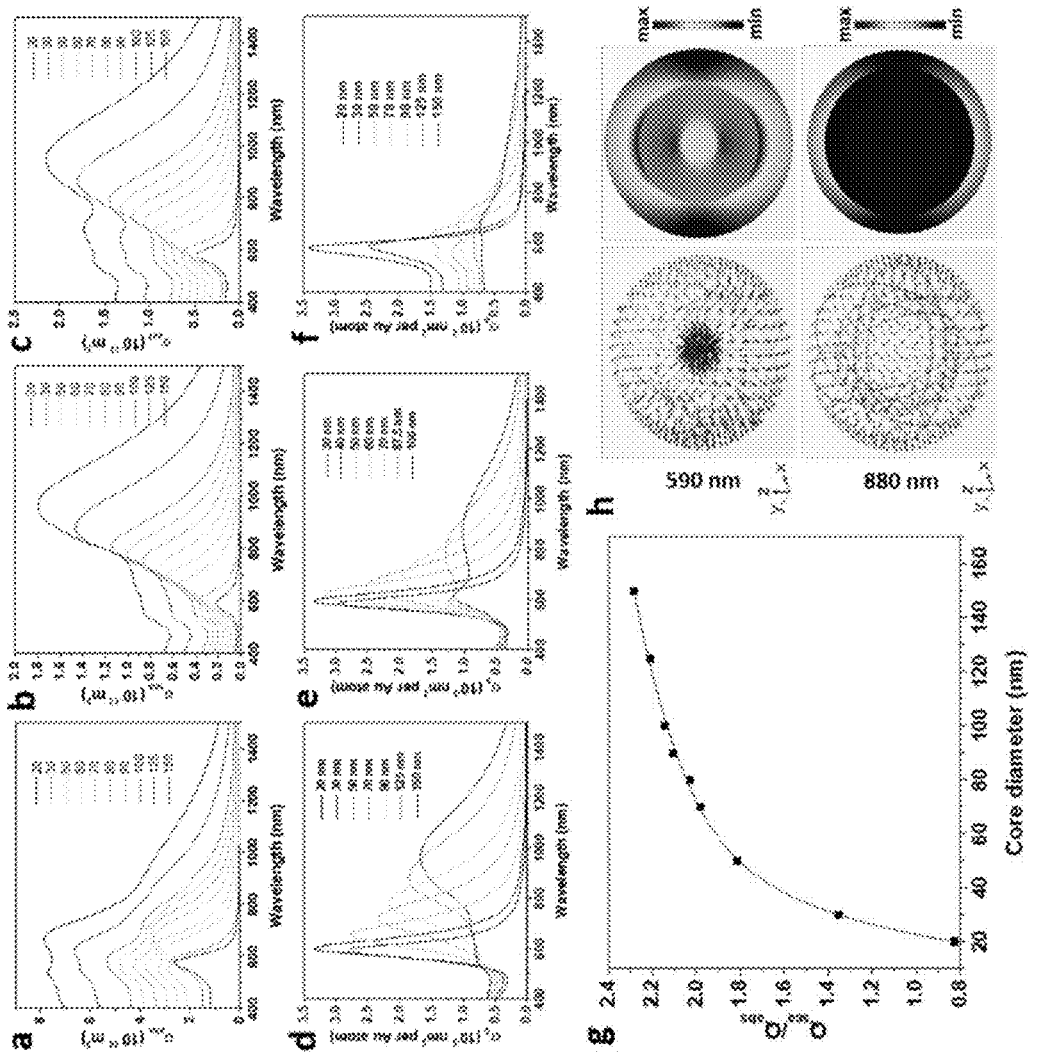
FIG. 6a-6h illustrate concept designs. Simulated absorption (FIG. 6a), scattering (FIG. 6b), and extinction (FIG. 6c) cross-sections of Au nanoshells. The thickness of Au nanoshells is 25 nm. The core size increases from 20 to 150 nm.

In accordance with an exemplary embodiment, the active tuning over the scattering of Au nanoshells is designed based on the fact that the Au nanoshells can selectively scatter light at a particular wavelength due to the LSPR while being almost "transparent" at off-resonance wavelengths. In accordance with an exemplary embodiment, a simulation shows that the resonant scattering of 25-nm thick Au nanoshells redshifts from 590 nm to 980 nm when their core size increases from 20 to 70, 125, and eventually 150 nm (FIGS. 6a-6d). Compared with solid nanoparticles of the same diameters (FIG. 6e, Au nanoshells exhibit higher scattering efficiency due to the enhancement at the multiple interfaces and broader tuning range due to their hybridized plasmon modes. The primary resonant scattering is far away from the strongest resonant absorption in Au nanoshells (FIG. 6f, which facilitates the scattering-based applications and leads to lowered optical loss at the resonant frequency. Also, the ratio between scattering efficiency and maximum absorption efficiency increases gradually with core sizes, and its value is greater than one in a broad spectrum (FIG. 6g). The surface scattering profiles of the Au nanoshells (left panels in FIG. 6h indicate strong scattering around the entire surface. The electric fields in Au nanoshells with larger cores (right panels in FIG. 6h have much lower magnitudes, further confirming their lower absorption at the on-resonance wavelength.

Figures 1A, 1B, 1C, 1D, 1E, 1F:
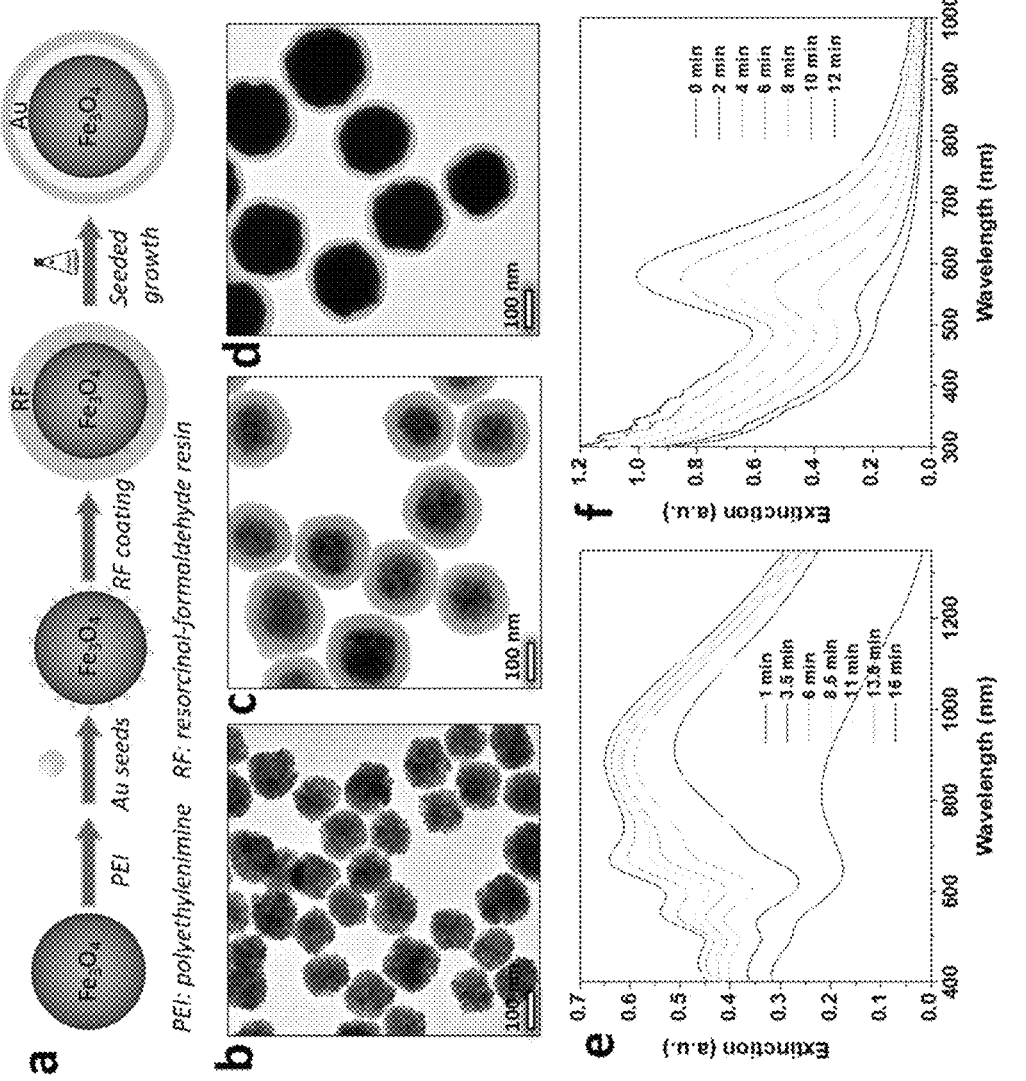
Figures 7A, 7B, 7C, 7D:
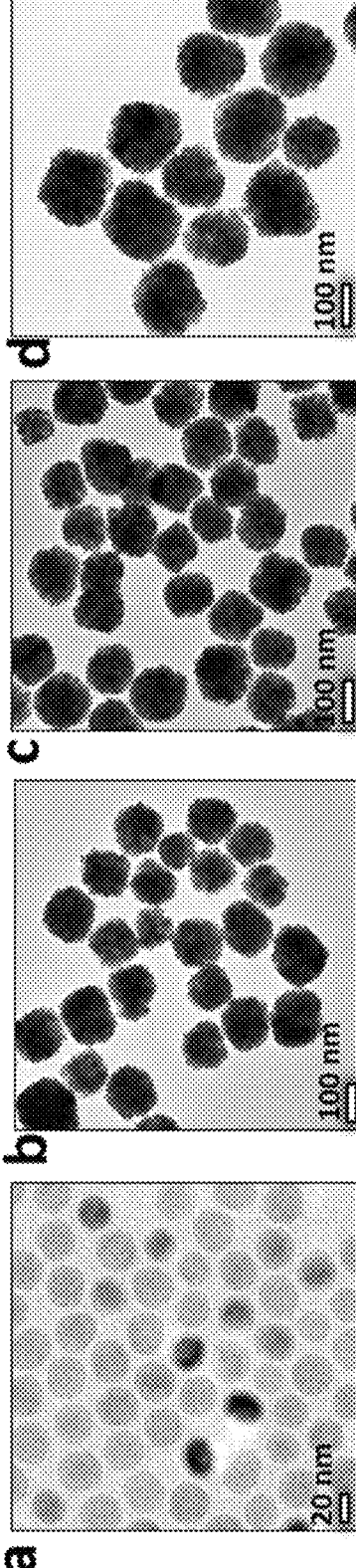
FIG. 7a-7d are TEM images of $Fe_3O_4$ nanoparticles of 20 nm (FIG. 7a), nm (FIG. 7b), 125 nm (FIG. 7c), and 150 nm (FIG. 7d).
Figures 8A, 8B, 8C:
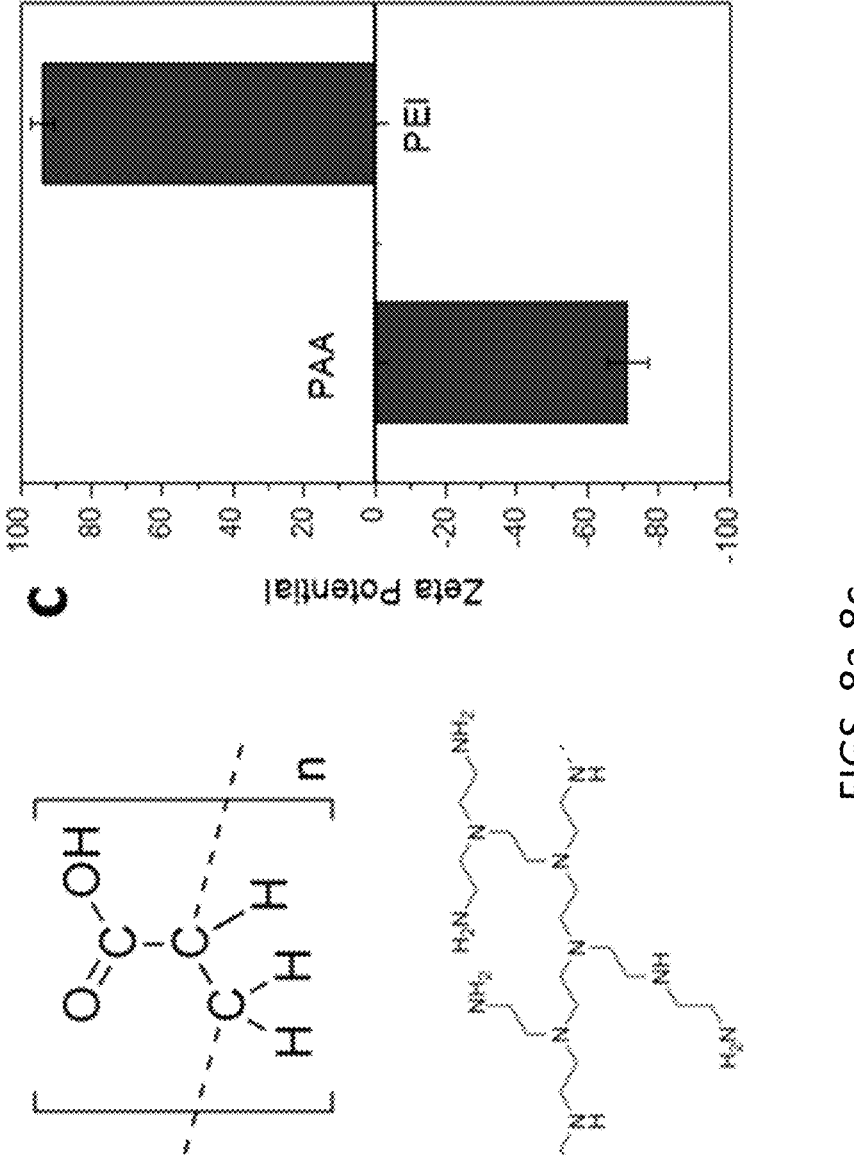
FIG. 8a-8c illustrate chemical structures of PAA (FIG. 8a) and branched PEI.
Figure 9:
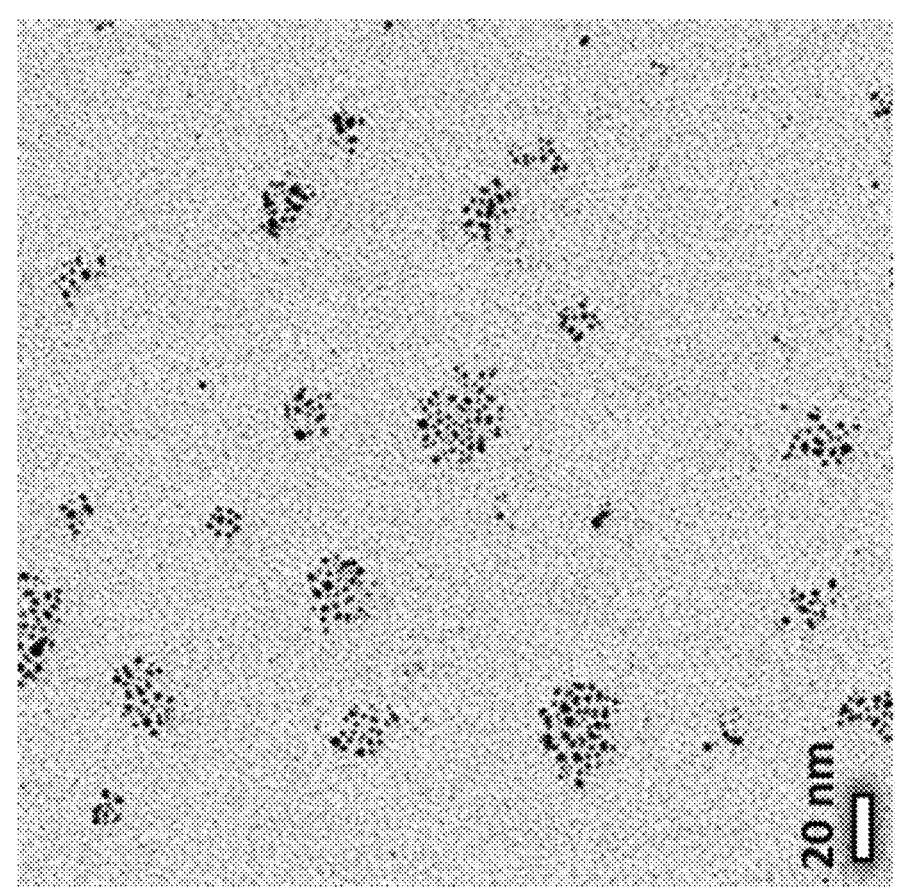
FIG. 9 is an illustration of a TEM image of Au seeds.

In accordance with an exemplary embodiment, the unique confined synthesis of Au nanoshells on magnetic nanoparticles is illustrated in FIG. 1a. Magnetite ($Fe_3O_4$) nanoparticles of different sizes from, for example, 20 nm to 150 nm were synthesized using polyacrylic acid (PAA) as capping ligands (FIGS. 7a-7b). FIG. 1b shows a typical TEM image of 125-nm iron oxide nanoparticles with uniform size and good dispersibility. They exhibited superparamagnetism as each nanoparticle consisted of a plurality of sub-10-nm grains. Branched polyethyleneimine (PEI) was introduced to the PAA-capped nanoparticle surface through electrostatic interaction, which was confirmed by a significant change in the zeta potential from −70 mV to +90 mV (FIG. 8a). Then, negatively charged Au seeds (approximately 2 nm, FIG. 9) capped by tetrakis(hydroxymethyl)phosphonium chloride were immobilized on the iron oxide surface through electrostatic adsorption, forming $Fe_3O_4$/Au nanoparticles, for further seeded growth. Afterward, the composited particles were overcoated with a layer of water-permeable and soft phenolic resin through based-catalyzed step-growth polymerization of resorcinol and formaldehyde (RF). The thickness of RF shells is 35 nm (FIG. 1c).

In accordance with an exemplary embodiment, one of the keys to the synthesis of uniform Au nanoshells is to ensure homogeneous deposition of Au atoms to multiple seeds and minimize the self-nucleation of free Au nanoparticles, which can be achieved by maintaining a low reduction rate. For example, $H_2O_2$ can be used as a mild reductant to support the seeded growth of Au nanoshell, as $H_2O_2$ has a pH-dependent standard reduction potential: 1.763 V in acidic solution and 0.867 V in alkaline solution. The reductant role of $H_2O_2$ in the alkaline condition is made possible by the formation of anion $HO_2^-$. Therefore, to avoid etching of Au seeds by $H_2O_2$, the pH of the growth solution was adjusted to slightly basic by adding sodium oleate so that $H_2O_2$ has a lower reduction potential than $AuCl_4^-$ (+0.93 V) and $AuCl_2^-$ (+1.15 V). Therefore, $H_2O_2$ can sustain the continuous, exclusive deposition of Au atoms on multiple seeds to form a conformal coating while its reducing power is carefully moderated to minimize self-nucleation during seeded growth. The seeded growth of Au nanoshells in alkaline conditions occurs in the following course:

$$H_2O_2 + OH^- = HO_2^- + H_2O \tag{1}$$

$$3HO_2^- + AuCl_4^- = Au + 3HO_2 \cdot + 4Cl^- \tag{2}$$

Figures 10A, 10B, 10C, 10D:
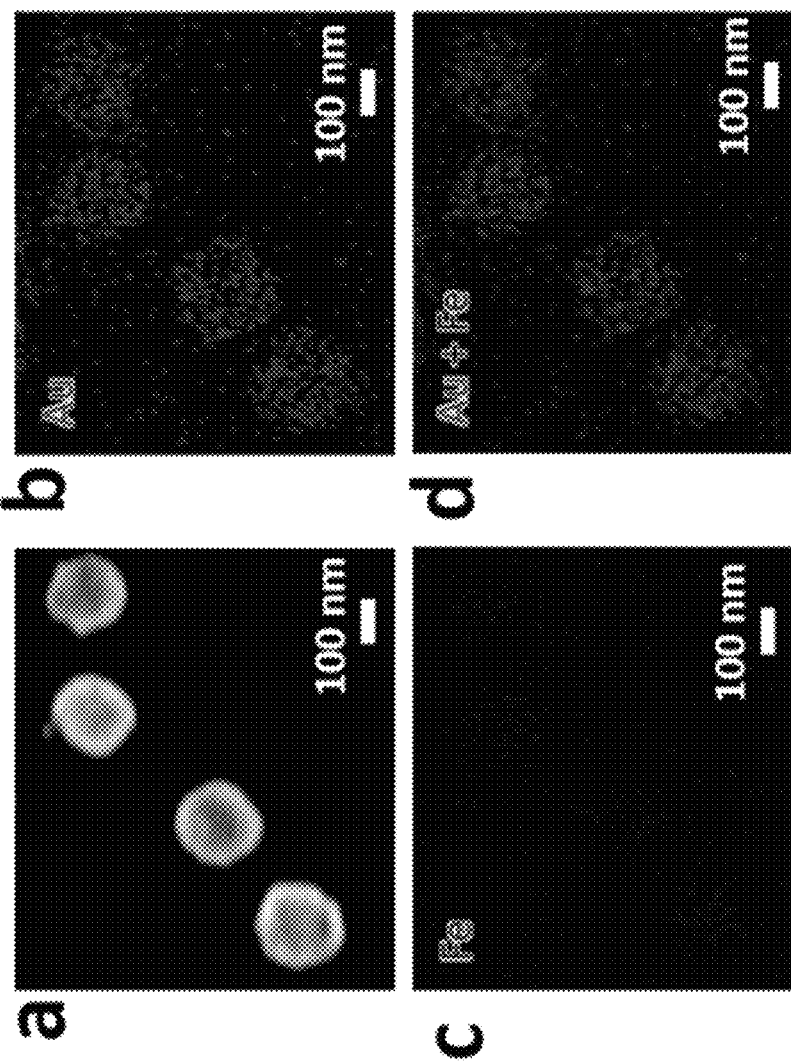
FIGS. 10a-10d illustrate in FIG. 10a a backscattered scanning electron microscopy of $Fe_3O_4$@Au@RF nanospheres with 125-nm cores. The corresponding elemental mapping of Au (FIG. 10b), Fe (FIG. 10c), and the merged images in FIG. 10d.
Figure 11A:
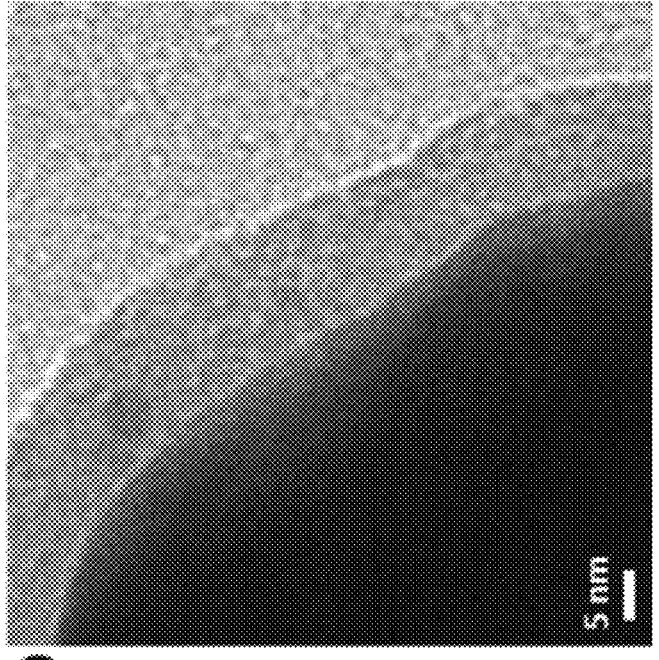
Figure 11B:
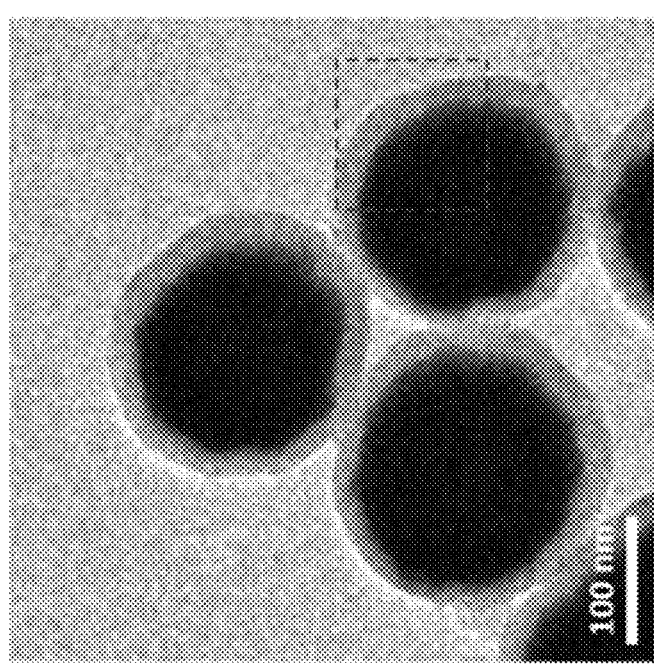
Figures 12A, 12B, 12C, 12D, 12E:
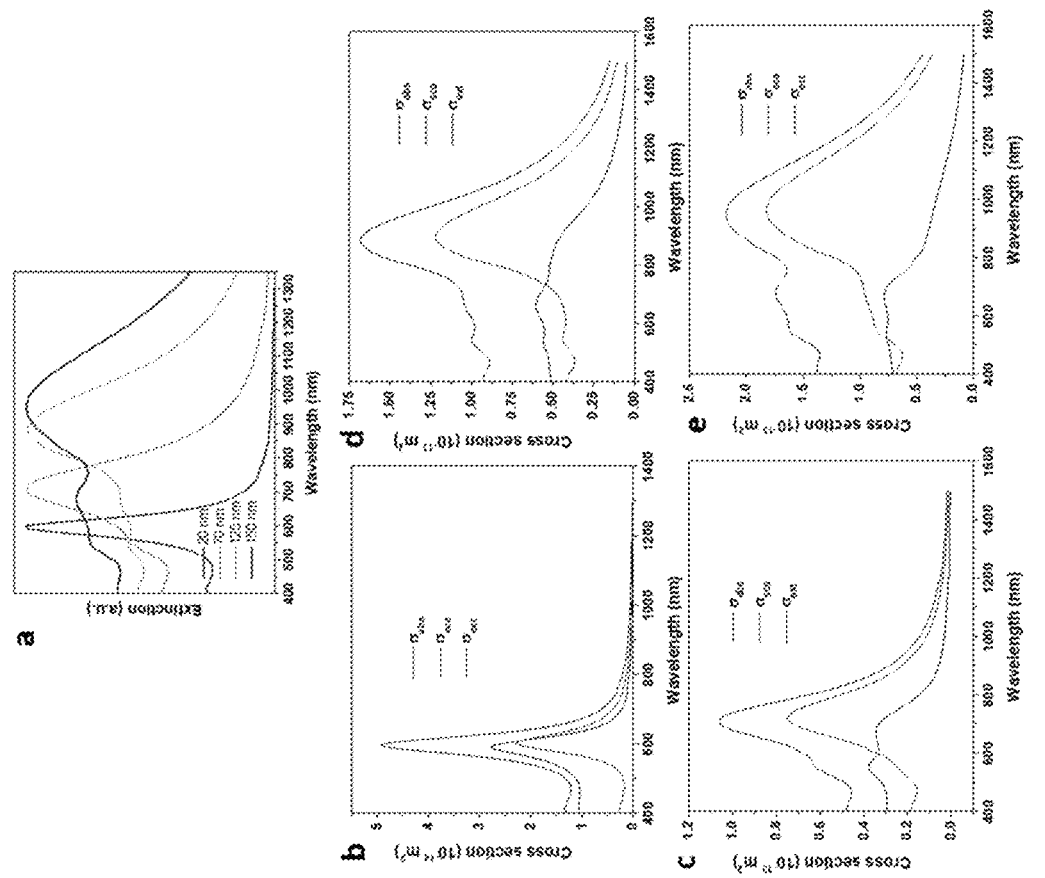
FIG. 12a-12e illustrated in FIG. 12a, a simulated extinction cross-sections of Au nanoshells with different core sizes. Simulated optical cross-sections of Au nanoshells with a core diameter of 20 nm (FIG. 12b), 70 nm (FIG. 12c), 125 nm (FIG. 12d) and 150 nm (FIG. 12e).

FIG. 1d shows the morphology of the particles after seeded growth, with complete Au nanoshells of ~25 nm in thickness. The back-scattered scanning electron microscopy (SEM) image in FIG. 10a demonstrates the core/shell structure of the nanoparticles. Because Au has a much higher atomic number than Fe and O, the Au nanoshells can scatter electrons more efficiently and thus appears much "brighter" than $Fe_3O_4$ cores. On the contrary, the RF shell cannot be observed in the back-scattering mode due to the small atomic number and low electron scattering efficiency of C, H, and O atoms. The elemental mapping results in FIGS. 10b-10d also help to explain the core/shell structures of the final products. A high-magnification TEM image is presented in FIGS. 11a and 11b, and the results clearly demonstrate the conformal coating of Au nanoshells rather than the presence of colloidal clusters at the $Fe_3O_4$—RF interfaces. Notably, the thickness of the RF shells decreased from the initial 35 nm to 18 nm during seeded growth, suggesting their expansion induced by continuous deposition of Au atoms.

The optical properties of Au nanoshells changed gradually during the seeded growth (FIG. 1e). At 1 min, one plasmon band appeared at 810 nm, indicating the successful growth of Au within the RF shells. As the reaction preceded, the band first red- and then blueshifted to 880 nm, which is consistent with the formation of thin shells followed by their gradual thickening. Notably, another plasmon peak appeared at 675 nm in addition to the initial one at 545 nm. In addition, as shown in FIGS. 6a-6h, calculations indicate that the plasmon band at 880 nm originates from the strong scattering of the Au nanoshells while the two bands at shorter wavelengths have absorption-dominated resonances. When a 20-nm $Fe_3O_4$ core was used, a continuous redshift of a single plasmon band from 525 to 600 nm was observed (FIG. 1f). The absence of the plasmon band at 530 nm in the final product suggests that there were no self-nucleation events during the seeded growth.

Figures 2A, 2B, 2C, 2D, 2E, 2F, 2G:
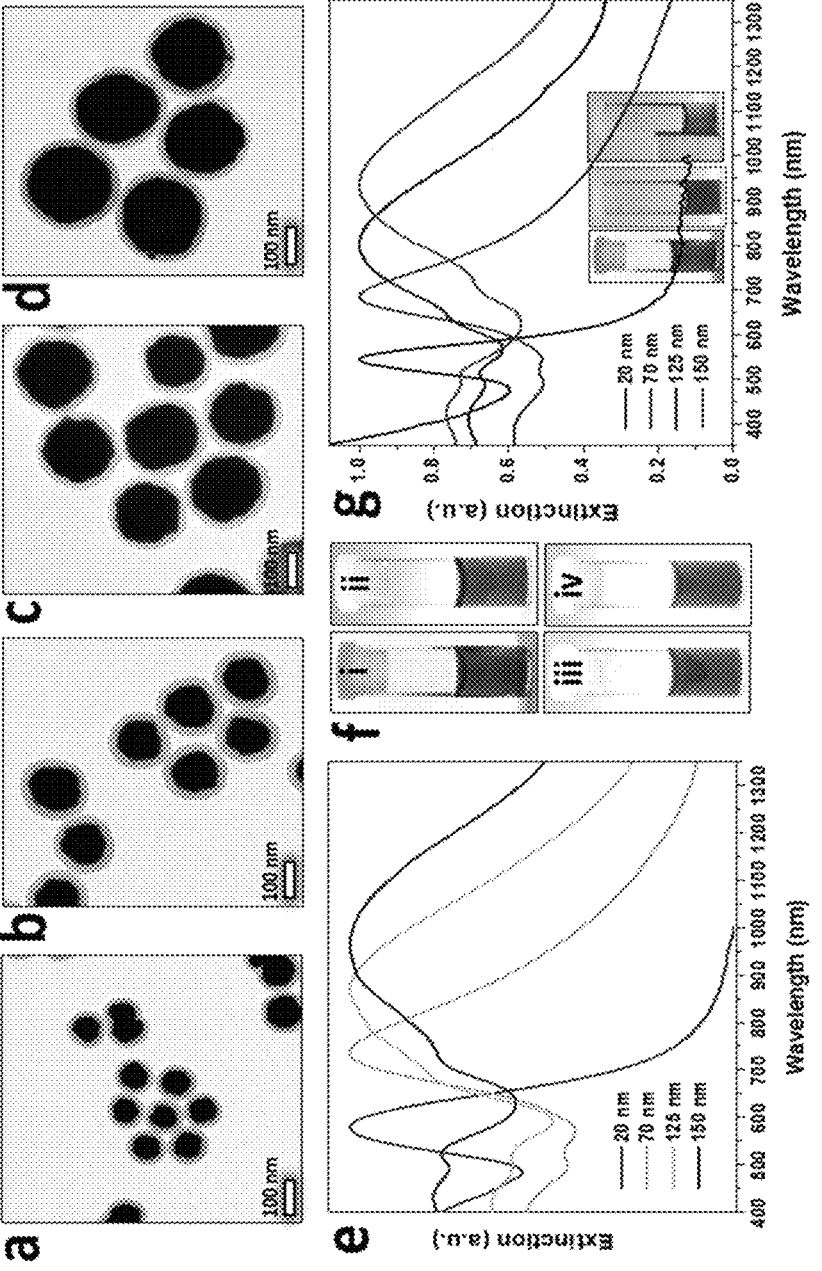
FIGS. 2a-2f are illustrations of tailorable resonant scattering of Au nanoshells. TEM images of $Fe_3O_4$@Au@RF nanospheres synthesized by using $Fe_3O_4$ nanospheres with a diameter of 20 nm (FIG. 2a), 70 nm (FIG. 2b), 125 nm (FIG. 2c), and 150 nm (FIG. 2d) as cores.
FIG. 2g illustrates UV-Vis spectra of as-synthesized Au nanoshells after etching away RF. Insets in FIG. 2g from left to right: $Fe_3O_4$@Au@RF, $Fe_3O_4$@Au and $Fe_3O_4$@Au solution exposed to a magnetic field pointing horizontally from left to right. The diameter of the $Fe_3O_4$ core is 20 nm.

In accordance with an exemplary embodiment, the current method can be readily used to produce Au nanoshells with different core sizes. FIGS. 2a-2d show some $Fe_3O_4$@Au@RF nanoparticles synthesized with $Fe_3O_4$ cores of 20, 125 and 150 nm, and 25-nm Au nanoshells. In their extinction spectra (FIG. 2d, it was observed a redshift of the plasmon bands from 585 to 730, 875 and 960 nm, and the corresponding change of solution color from blue to green and brown (FIG. 2f). The measured extinction spectra of Au nanoshells are consistent with the simulated spectra in FIGS. 12a-12e, indicating their high quality and well-defined plasmonic properties. Considering the need for accessible metal surfaces in many plasmonic applications, particularly in biosensing, imaging, and SERS, a reliable etching process was further developed that could be used to remove the RF layers in NaOH solutions at 80° C. while retaining the excellent plasmonic properties of the hybrid particles. For Au nanoshells containing 20-nm cores, a blueshift from 600 nm to 540 nm was observed (FIG. 2g) due to the decreased surrounding refractive index from approximately 1.5 to 1.33, along with a color change from blue to red. The sharper peak confirms the removal of RF and the well-retained good dispersity of the Au nanoshells (FIGS. 13a-13g). The $Fe_3O_4$@Au nanoparticles could be magnetically separated from the solution when a magnet was placed near the solution (insets in FIG. 2g).

Figures 3A, 3B, 3C, 3D, 3E, 3F, 3G, 3H:
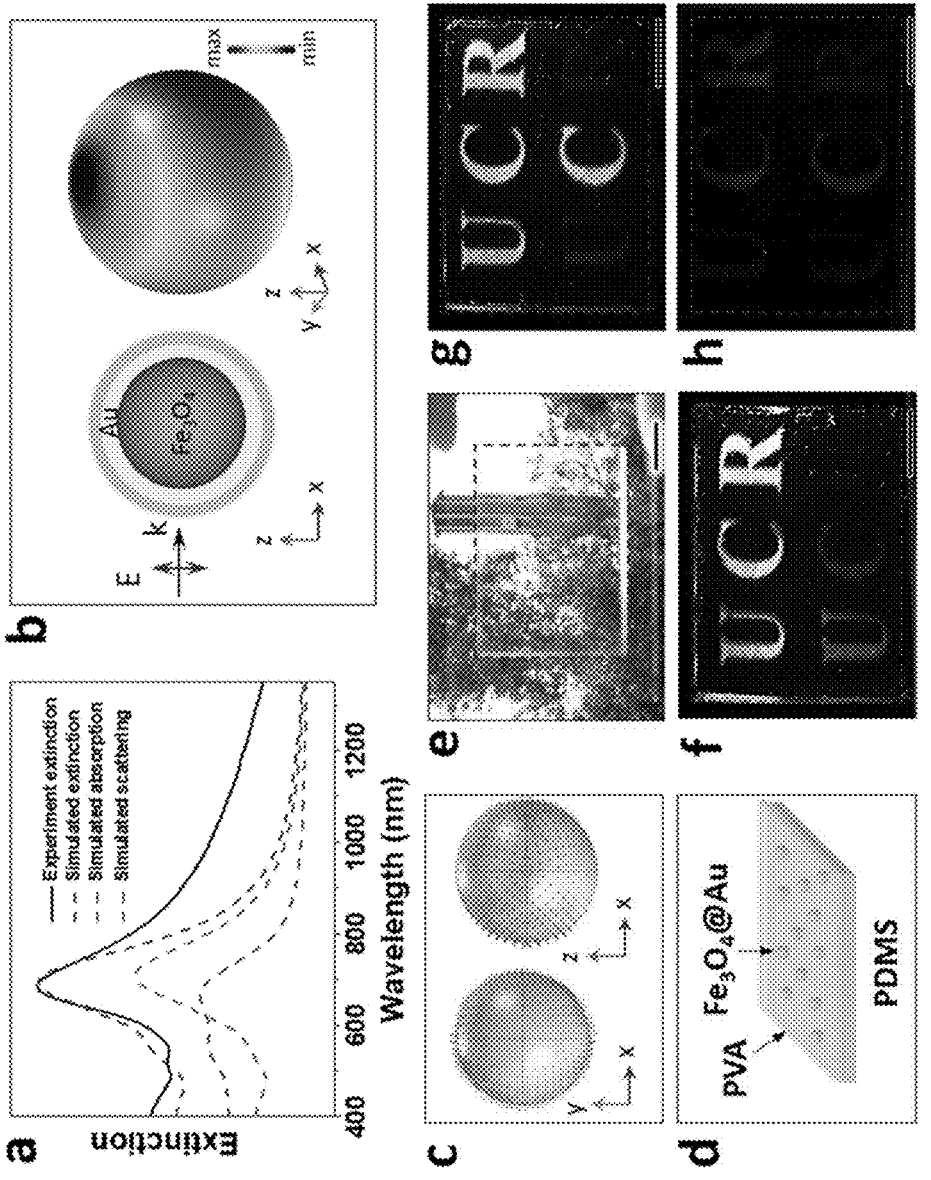
FIGS. 3a-3h illustrate resonant scattering of Au nanoshells for transparent displays.
Figure 14A:
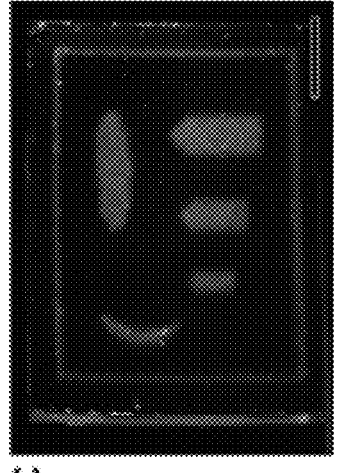
FIGS. 14a-14c illustrate in FIG. 14a the "letters" projected on the transparent screens by a commercial projector. Specifically, the "UCR" in the top row is white in color. The letters "UCR" in the bottom row are red, green, and blue from left to right, respectively.
Figure 14B:
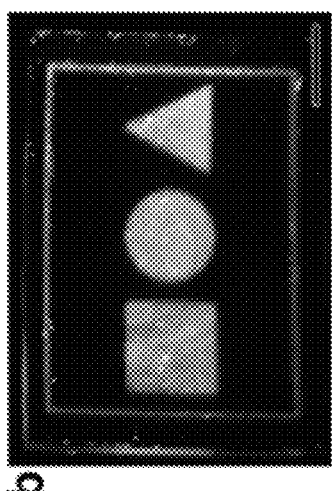
Figure 14C:
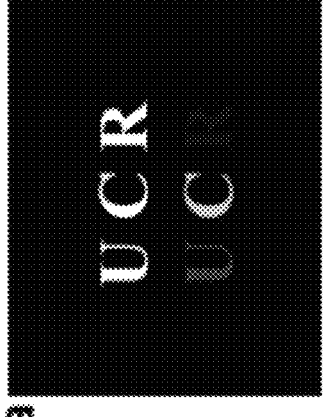

This robust and flexible synthesis process allows convenient turning of the optical scattering of Au nanoshells, offering great opportunities for the fabrication of scattering-based applications. Simulations demonstrate that $Fe_3O_4$@Au nanoparticles with 70-nm cores and 25-nm shells exhibit much stronger resonant scattering than absorption (FIG. 3a). At the resonant wavelength, the scattered field of the Au nanoshells is similar to the radiation pattern of a typical dipole antenna (FIG. 3b). The Poynting vectors and localized electric field distribution in FIG. 3c further confirm the wide-angle scattering of Au nanoshells. To take advantage of the intriguing optical property, Au nanoshells were incorporated into a transparent polymer matrix with a final $Fe_3O_4$@Au concentration of approximately 0.005 mg/mL and then spin-cast the mixture on a PDMS substrate (FIG. 3d. Upon drying, the film appeared to be highly transparent under ambient lighting (FIG. 3e). Interestingly, when the film was illuminated with intense white light, it appeared to be red if hybrid nanoparticles containing 70-nm cores were used (FIG. 3f, top row) and green in the case with 20-nm cores (FIG. 3g, top row), demonstrating the selective scattering depending on the resonant frequency of the Au nanoshells. In both cases, a commercial image projector was used to illuminate the films with three white letters at the top row and three primary colored (blue, green, and red) letters at the bottom row, as illustrated in FIGS. 14a-14c. In FIG. 3f, the film could display red letters (on the top row) when illuminated by letter-containing white light because Au nanoshells with 70-nm cores have a resonant wavelength at 685 nm and preferentially scatter red light. In FIG. 3g, the complex film displays green letters because the resonant wavelength (approximately 540 nm) of the embedded Au nanoshells is in the green color gamut (500 nm to 565 nm). More importantly, under monochromic light illumination, the films could display corresponding patterns only when the wavelength of the projected light and the plasmonic band matched. As shown in the bottom rows in FIGS. 3f and 3g, the films made from Au nanoshells with 20-nm and 70-nm cores can selectively display green and red letters, respectively, while in the mismatched cases, letters are not easily noticeable. In contrast, the image could barely be observed on a pure polymer film without Au nanoshells under the same projected light due to the lack of strong scattering (FIG. 3h). In accordance with an exemplary embodiment, these transparent films may find interesting applications such as anti-counterfeiting devices or information displays.

Figures 4A, 4B, 4C:
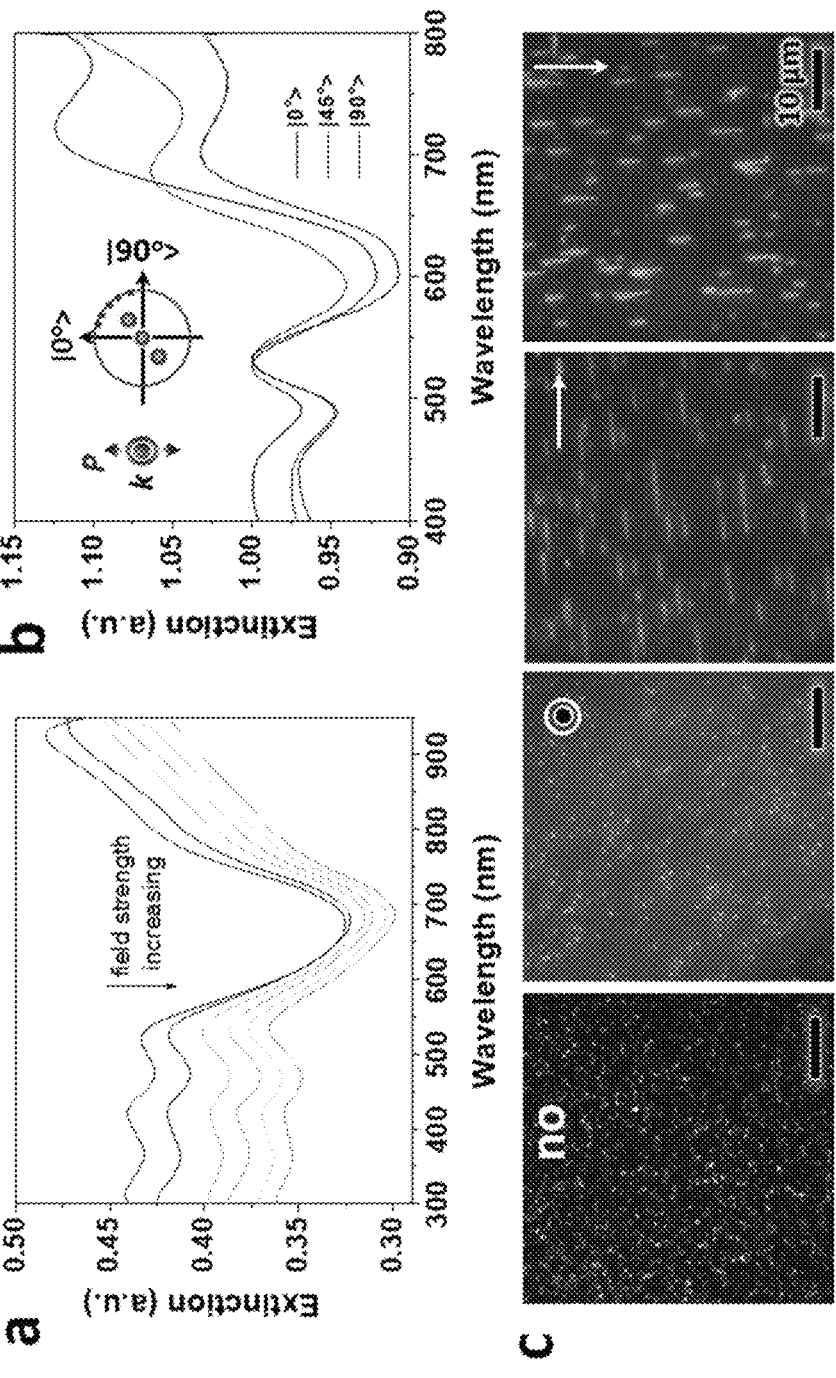
FIGS. 4a-4c illustrate plasmon coupling of Au nanoshells enabled by the magnetic assembly of $Fe_3O_4$@Au@RF nanospheres into plasmonic chains.
Figure 15:
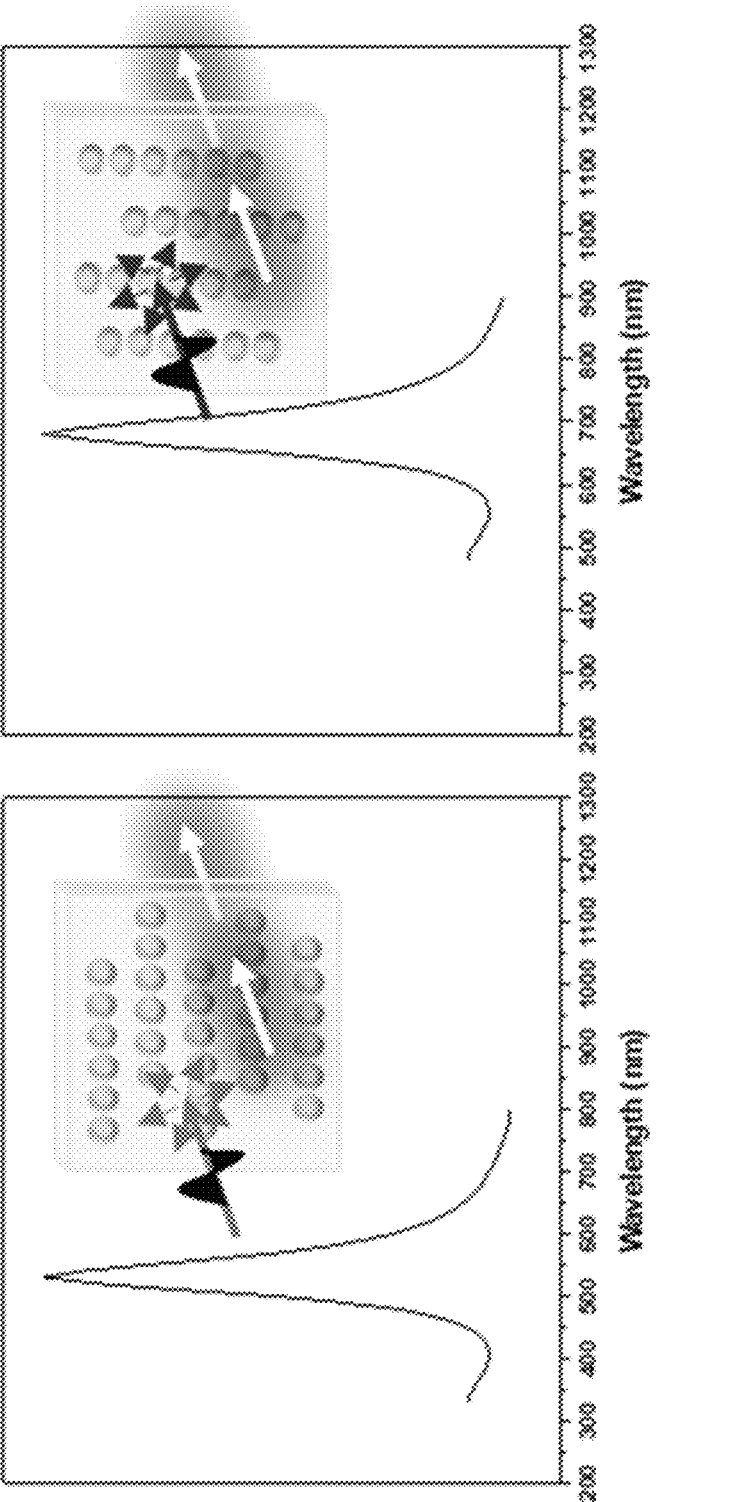
FIG. 15 is a schematic illustration of the active tuning of the plasmon coupling of Au shells enabled by the magnetic assembly of $Fe_3O_4@Au@RF$ nanoparticles. Specifically, changing the chain orientation relative to the light polarization will alter the plasmonic excitation of the 1D nanochains, which further leads to the changes of scattering properties of the chains.
Figures 16A, 16B, 16C, 16D:
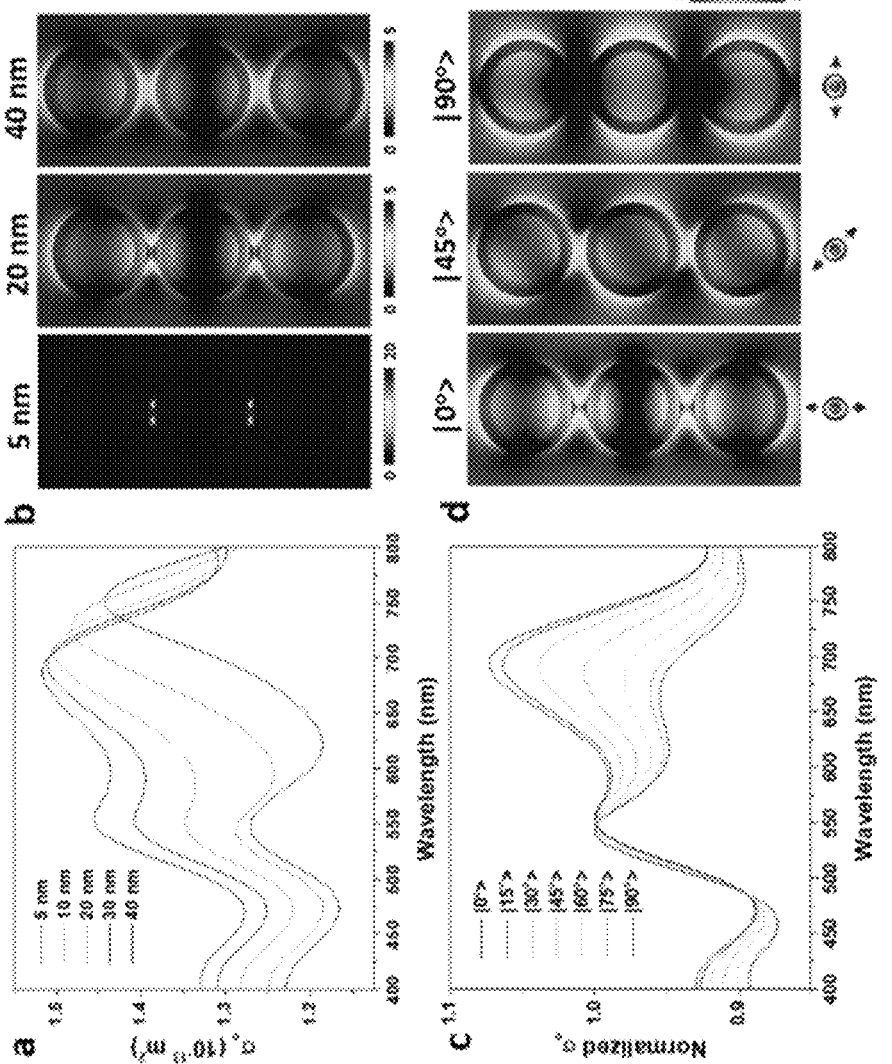
FIGS. 16a-16d illustrate in FIG. 16a is a simulated extinction spectra of the plasmonic chain under different particle separation.

The integration of magnetic and plasmonic properties in the core-shell structures makes it possible to actively tune the plasmon coupling of Au nanoshells by their magnetic assembly into 1D nanochains (FIG. 15). The optical cross-sections of the assembled chains under different interparticle separations and orientations was first calculated. For plasmonic chains containing Au nanoshells with 50-nm cores, a redshift of the coupling band could be observed as the interparticle separation decreases, for example, from 40 nm to 5 nm, along with a great increase in the enhancement of localized electric fields within the gaps (FIGS. 16a and 16b). On the other hand, for nanochains with an interparticle separation of 30 nm, the intensity of the peaks at approximately 695 nm decreased when the angle between chain orientation and polarization changed from 0° to 90° (FIGS. 16c and 16d). To verify the plasmon coupling of Au nanoshells, the extinction spectra of $Fe_3O_4$@Au@RF was measured under different magnetic fields. The peak position of coupling bands slightly redshifted because of the reduced interparticle separation when the field strength increased (FIG. 4a). In FIG. 4b, the coupling peak reached a maximum value when a magnetic field parallel to the polarization of the incident light (0°) was applied. A gradual increase of the angle weakened the coupling strength so that the peak intensity of the coupling band at approximately 725 nm decreased.

Figure 17:
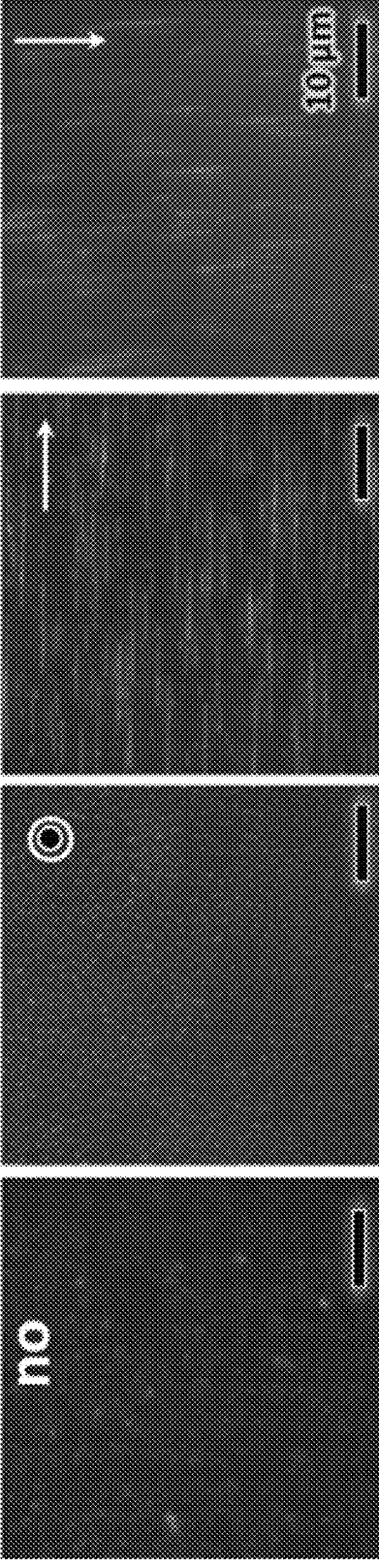
FIG. 17 are POM images of $Fe_3O_4$/Au@RF dispersions under different magnetic fields. White arrows indicate the directions of the applied magnetic fields.

The magnetic assembly and orientational control represent a reliable way to actively regulate the coupled resonant scattering of Au nanoshells. As shown in the optical microscopic images in FIG. 4c, bright dots in the absence of any magnetic field due to the scattering of individual nanoparticles was only observed. When a magnetic field parallel to light polarization was applied, 1D chains with bright red color formed immediately. The extremely fast response is ascribed to the high saturation magnetization of the $Fe_3O_4$ cores. When magnetic fields were removed, the chains disassembled due to surface electrostatic repulsion of the RF shells, which enabled the reversible and dynamic tuning of the plasmon coupling of Au nanoshells. Interestingly, the apparent color of the 1D chains was dependent on their orientations under linearly polarized light. When the orientation of the chains was parallel to the light polarization, bright red color was observed. Under the other two perpendicular orientations, the red color disappeared. To further confirm the plasmonic origin of the color, control experiments using nanoparticles before seeded growth as the building blocks were carried out. As shown in FIG. 17, no obvious color was observed under the three typical orientations. Therefore, it is reasonable to conclude that the perceived red color of 1D chains is from the coupled resonant scattering of the Au nanoshells.

Figures 5A, 5B, 5C, 5D:
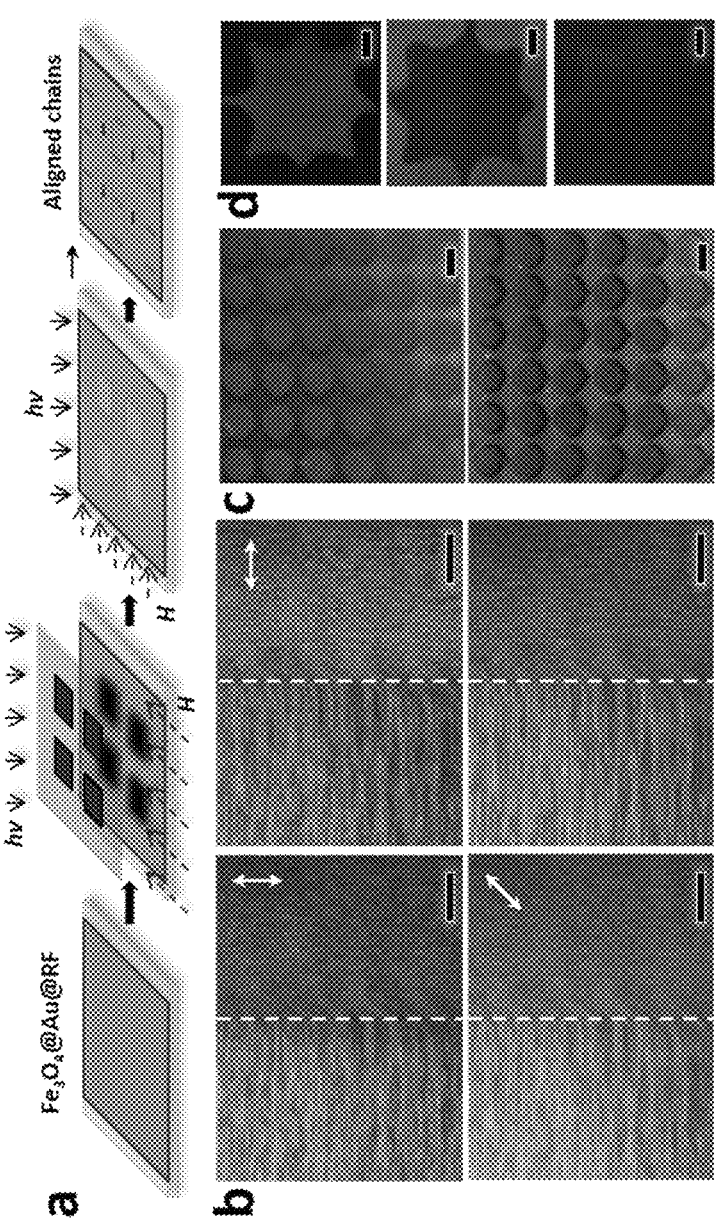
FIGS. 5a-5d illustrate coupled resonant scattering of Au nanoshells enabled by the magnetic assembly of $Fe_3O_4$@Au@RF nanospheres into plasmonic chains.

Compared with the previous methods for actively tuning the coupling of plasmonic nanostructures, such as changing the surrounding dielectrics or interparticle separations by chemical and electronic doping, the magnetic assembly approach has advantages of fast response, full reversibility, and chemical-free control. The magnetic anisotropy of 1D plasmonic chains also facilitates the control over the orientation of the assemblies. Therefore, color-changing anti-counterfeiting devices could be fabricated by fixing the plasmonic chains with pre-designed orientations in a photocurable polymer (FIG. 5a). As shown in optical microscopic images in FIG. 5b, under vertically polarized light, the right area appeared red due to the coupled resonant scattering of Au nanoshells while the left area was brown. When rotating the polarizer to a horizontal position, the color in these two regions switched. Moreover, the color contrast in the two regions disappeared at a relative angle of 45° or in the absence of a polarizer because the plasmonic excitation of 1D chains was the same in both cases. FIGS. 5c and 5d exhibit two patterns created by the multi-step lithography method. The color contrast of perceived patterns could be simply altered by switching the polarization of the incident light, which can be potentially used for anti-counterfeiting or information encryption.

In summary, an unconventional synthesis approach to Au nanoshells has been developed by confining the seeded growth of Au within the hard-soft interface between the $Fe_3O_4$ core and the deformable RF shell. The growth of the Au nanoshells does not require limiting gaps or spaces but instead relies on the elastic deformation of the cross-linked RF shells. The as-prepared Au nanoshells have excellent plasmonic properties, which can be readily tuned from visible to NIR regions by simply increasing the core sizes. This space-free confined growth can be potentially extended to synthesizing other core-shell nanostructures, where the growth is preferably parallel rather than perpendicular to the core surface. The well-defined, highly tailorable optical properties of the Au nanoshells allow the successful development of unique transparent displays and anti-counterfeiting colorimetric devices. Further, the nanoscale magnetic assembly strategy offers many advantages in actively tuning the plasmon coupling of nanostructures, including instantaneous response, chemical-free remote control, and full reversibility.

Synthesis of Au Shells

Chemicals: All chemicals are used directly without further purification. Ethanol was purchased from Decon Labs. Iron chloride (III) hexahydrate, tetraethyl orthosilicate (TEOS), polyacrylic acid (PAA, MW=1800), sodium hydroxide, polyvinylpyrrolidone (PVP, MW=10000), resorcinol (R), formaldehyde f, 2-Hydroxy-2-methylpropiophenone, polyvinyl alcohol (PVA), 2-Hydroxy-2-methylpropiophenone and Tetrakis(hydroxymethyl)phosphonium chloride (THPC) were bought from Sigma-Aldrich. Ammonium hydroxide and hydrogen peroxide ($H_2O_2$) were purchased from Fisher Scientific. Chloroauric (III) acid trihydrate ($HAuCl_4 \cdot 3H_2O$) and ethylene glycol (EG) was from Acros Organics. Acrylamide (AM) and N,N'-Methylenebisacrylamide (BIS) was purchased from Fluka. Oleic acid sodium salt (NaOL) was purchased from TCI AMERICA. SYLGARD 184 silicone elastomer curing agent and SYLGARD 184 silicone elastomer base were purchased from Dow silicone corporation. Acrylamide (AM) and N,N'-Methylenebisacrylamide (BIS) were purchased from Fluka.

Synthesis of $Fe_3O_4$ nanoparticles: Colloidal particles of $Fe_3O_4$ nanoparticles with tunable size were synthesized. The reaction was carried in the solution phase at elevated temperature. A stock solution was prepared by dissolving 50 mmol NaOH in 20 mL of DEG, which was heated at 120° C. for 1 hour under the protection of nitrogen. The solution was kept at 70° C. as a stock solution. In a typical synthesis, PAA (4 mmol) and $FeCl_3$ (0.4 mmol) were dissolved in DEG (17 mL), and the mixture was heated to 22° C. for 30 min under the protection of nitrogen. A certain amount of stock solution was injected rapidly. The mixture was heated at 220° C. for another one hour. The volumes of stock solutions were 1.7, 1.75, and 1.8 mL for the synthesis of $Fe_3O_4$ nanoparticles with an average diameter of 70, 125, and 150 nm, respectively. The obtained $Fe_3O_4$ nanoparticles were washed by deionized water several times and dispersed in 20 mL of water.

PEI modification: For PEI modification, 5 mL (0.25 batch) of an aqueous solution of $Fe_3O_4$ nanoparticles was added into 30 mL of PEI solution (20 mg/mL, Mw=800) under sonication. The mixed solution was agitated by vortex overnight. To get rid of magnetic field-induced aggregation, magnetic stirring was not suggested during PEI modification. After that, $Fe_3O_4$ nanoparticles were washed with water three times and then dispersed in 5 mL of water.

Au seed preparation: THPC (12 µL) and NaOH (250 µL, 2M) were added into 45 mL water. After stirring for 5 min, 2 mL of HAuCl4 was added. The Au seeds (Aus) solution was stocked in the dark for further attachment.

Au seed attachment: To 30 mL of Au seed solution, 5 mL of $Fe_3O_4$ nanoparticle solutions after PEI modification was added slowly under sonication. The mixed solution was agitated for about one hour. Excess Au seed was removed by centrifugation. Au seed was attached to the surface of $Fe_3O_4$ nanoparticles due to the electrostatic interactions, forming $Fe_3O_4$/Aus nanoparticles. They were further washed by water three times and then dispersed in 10 mL of water.

RF coating: PVP modification was first carried out before RF coating. In a typical process, a 10 mL solution of $Fe_3O_4$/Aus was added into 30 mL of PVP solution (5 mg/mL) under sonication. The solution was agitated by vortex overnight. The solution was washed by water three times to remove excess PVP. Finally, they were dispersed in 28 mL of water for RF coating. In a based-catalyzed step-growth polymerization, 20 mg R and 28 µL of F were added in sequence. 100 µL of ammonia solution (2.8%) was added into the solution. The reaction was first sonicated for 1 hour and then transferred into a 50 mL round bottom flask.

The reaction was kept at 100° C. for 3 hours in order to further condense RF resins and increase their cross-linking ratios. After cooling down to room temperature, the solution was washed three times by water. Then obtained $Fe_3O_4$/Aus@RF was finally dispersed in 2 mL of water.

Seed-mediated growth of Au nanoshells: In a typical process, 500 µL of PVP (50 mg/mL, Mw=40000), 100 µL of NaOL (10 mM), 20 µL of $HAuCl_4$ (0.25 M) and 50 µL of $H_2O_2$ were added into 7.5 mL of deionized water in sequence. Then, 25 µL of $Fe_3O_4$/Aus@RF solution was added. The reaction occurred at room temperature for 30 min. The product was washed by deionized water three times and dispersed in deionized water for characterization.

Etching RF shells: The solutions of $Fe_3O_4$@Au@RF nanoparticles were first dispersed in 2 M of NaOH solutions. To improve dispersibility of colloidal particles, the reaction occurred under the presence of 0.5 M PVP. After incubating at 80° C. overnight, $Fe_3O_4$@Au nanoparticles were washed by DI water for three times. The removal of RF also led to a blueshift from 730 nm to 685 nm in the plasmon band of Au shells synthesized with 70-nm cores (FIG. S8g). Against a bright background, the perceived color in the colloidal dispersion was complementary to the plasmonic extinction. Therefore, the color turned from green to light blue (left two panels in the inset of FIG. 13g). Interestingly, against a dark background, both the solutions before and after removing RF shells appeared red (right two panels in FIG. 13g), which is ascribed to their strong scattering of red light between 622 and 770 nm.

Characterization: Extinction spectra were measured by Ocean Optics HR2000 spectrometer. TEM images were taken on Tecnai 12 transmission electron microscope at 120 kV. Dark-field optical macroscopic images were taken using A Zeiss AXIO Imager optical microscope. The SEM images were taken on ThermoFisher Scientific (formerly FEI/Philips) NNS450 scanning electron microscope with a back-scattering electron detector. The elemental mapping was performed at 50 kV.

Fabrication of Plasmonic Films

Preparation of PVA-Au composite films: PDMS film served as a transparent substrate for the PVA-plasmonic composite films. Silicone elastomer curing agent and silicone elastomer base were thoroughly mixed with a mass ratio of 1 to 10. The mixture was placed at ambient conditions for 2 hours to remove the air bubble inside the viscous solution. Then, it was cured at 60° C. for two hours. 10% PVA solution was first prepared by dissolving PVA into deionized water under sonication. Then a certain amount of PVA solution was added into the Au shell solution with a final concentration of about 0.005 mg/mL. The obtained mixture solution was spin-casted on a PDMS substrate. To form a uniform thin PVA film, the PDMS substrate was first treated by plasma for 20 min. The casted film was dried in a vacuum at room temperature.

Preparation of anti-counterfeiting films: 2-Hydroxy-2-methylpropiophenone serves as a photoinitiator. AM is monomer and BIS is the cross-linking agent. In a typical process, 250 mg of AM, 14 mg of BIS and 3 µL of 2-Hydroxy-2-methylpropiophenone were added in 1 mL of DEG. Au shell was first precipitated by centrifugation and then dispersed in the DEG solution. The mixture solution was sandwiched between glass slides and then was exposed to UV light (254 nm) for 1 min. A photomask with a pre-designed pattern was placed atop the sample, followed by applying a magnetic field ($B_1$). After the first UV exposure, 1D plasmonic chains with parallel alignment to external fields were fixed in the uncovered areas. The photomask was then removed, and a second UV exposure was applied to polymerize the remaining parts of the film under a horizontal magnetic field ($B_2$). The magnetic alignment was achieved by placing the mixture into the center of two identical permanent magnets. The field strength was measured to be 25 mT (250 G).

Analyzing Optical Properties of Au Nanoshells by Finite Element Method

Calculating optical cross-section of single Au nanoshell: The computation of optical cross-section and efficiency is achieved based on the finite element method (Comsol Multiphysics). A sphere with core-shell-shell geometry is modeled to mimic the $Fe_3O_4$@Au@RF nanostructures. The refractive index of RF is identified as 1.5. The domain of Au is defined by the built-in "Au" materials. Their physical properties, like the wavelength-dependent complex refractive index, have been fully described in the material library of Comsol Multiphysics. For the $Fe_3O_4$ domain, their refractive index is also wavelength-dependent and has a complex value with the real part determining the scattering properties and imaginary part determining the absorption of $Fe_3O_4$ material. To analyze the size-dependent opportunities of Au shell (FIGS. 1a-1f), the thickness of Au and RF shell is 25 nm and 20 nm, respectively. Instead, the diameter of the magnetic core increases from 20 nm to 30 nm, 50 nm, 70 nm, 80 nm, 90 nm, 100 nm, 125 nm, and 150 nm. Their scattering ($\sigma_{sca}$), absorption (Gabs) and extinction ($\sigma_{ext}$) cross-sections are calculated by solving the Maxwell equations in Comsol Multiphysics. The optical coefficients (Q) of Au shell, like scattering and absorption coefficient, were calculated by dividing the corresponding optical cross-sections by the physical cross-sections of the Au shell. The correlation between them can be expressed as $\sigma = Q\pi r^2$, where r is the radius of the Au shell.

Analyzing the coupling between Au nanoshells within plasmonic chains; The optical cross-sections of plasmonic chains were also calculated by the finite element method. In geometry, a 1D chain containing Au shells with well-controlled interparticle separation and orientation was first created in the Comsol Multiphysics. Then, the $\sigma_{ext}$ was calculated and normalized to a number of Au shells in the 1D chains.

Synthesis of Au Shells

Chemicals: All chemicals are used directly without further purification. Ethanol was purchased from Decon Labs. Iron chloride (III) hexahydrate, tetraethyl orthosilicate (TEOS), polyacrylic acid (PAA, MW=1800), sodium hydroxide, polyvinylpyrrolidone (PVP, MW=10000), resorcinol (R), formaldehyde f, 2-Hydroxy-2-methylpropiophenone, polyvinyl alcohol (PVA), 2-Hydroxy-2-methylpropiophenone and Tetrakis(hydroxymethyl)phosphonium chloride (THPC) were bought from Sigma-Aldrich. Ammonium hydroxide and hydrogen peroxide ($H_2O_2$) were purchased from Fisher Scientific. Chloroauric (III) acid trihydrate ($HAuCl_4 \cdot 3H_2O$) and ethylene glycol (EG) was from Acros Organics. Acrylamide (AM) and N,N'-Methylenebisacrylamide (BIS) was purchased from Fluka. Oleic acid sodium salt (NaOL) was purchased from TCI AMERICA. SYLGARD 184 silicone elastomer curing agent and SYLGARD 184 silicone elastomer base were purchased from Dow silicone corporation. Acrylamide (AM) and N,N'-Methylenebisacrylamide (BIS) were purchased from Fluka.

Synthesis of $Fe_3O_4$ nanoparticles: Colloidal particles of $Fe_3O_4$ nanoparticles with tunable size were synthesized. The reaction was carried in the solution phase at elevated temperature. A stock solution was prepared by dissolving 50 mmol NaOH in 20 mL of DEG, which was heated at 120°

C. for 1 hour under the protection of nitrogen. The solution was kept at 70° C. as a stock solution. In a typical synthesis, PAA (4 mmol) and $FeCl_3$ (0.4 mmol) were dissolved in DEG (17 mL), and the mixture was heated to 22° C. for 30 min under the protection of nitrogen. A certain amount of stock solution was injected rapidly. The mixture was heated at 220° C. for another one hour. The volumes of stock solutions were 1.7, 1.75, and 1.8 mL for the synthesis of $Fe_3O_4$ nanoparticles with an average diameter of 70, 125, and 150 nm, respectively. The obtained $Fe_3O_4$ nanoparticles were washed by deionized water several times and dispersed in 20 mL of water.

PEI modification: For PEI modification, 5 mL (0.25 batch) of an aqueous solution of $Fe_3O_4$ nanoparticles was added into 30 mL of PEI solution (20 mg/mL, Mw=800) under sonication. The mixed solution was agitated by vortex overnight. To get rid of magnetic field-induced aggregation, magnetic stirring was not suggested during PEI modification. After that, $Fe_3O_4$ nanoparticles were washed with water three times and then dispersed in 5 mL of water.

Au seed preparation: THPC (12 μL) and NaOH (250 μL, 2M) were added into 45 mL water. After stirring for 5 min, 2 mL of $HAuCl_4$ was added. The Au seeds (Aus) solution was stocked in the dark for further attachment.

Au seed attachment: To 30 mL of Au seed solution, 5 mL of $Fe_3O_4$ nanoparticle solutions after PEI modification was added slowly under sonication. The mixed solution was agitated for about one hour. Excess Au seed was removed by centrifugation. Au seed was attached to the surface of $Fe_3O_4$ nanoparticles due to the electrostatic interactions, forming $Fe_3O_4$/Aus nanoparticles. They were further washed by water three times and then dispersed in 10 mL of water.

RF coating: PVP modification was first carried out before RF coating. In a typical process, a 10 mL solution of $Fe_3O_4$/Aus was added into 30 mL of PVP solution (5 mg/mL) under sonication. The solution was agitated by vortex overnight. The solution was washed by water three times to remove excess PVP. Finally, they were dispersed in 28 mL of water for RF coating. In a based-catalyzed step-growth polymerization, 20 mg R and 28 μL of F were added in sequence. 100 μL of ammonia solution (2.8%) was added into the solution. The reaction was first sonicated for 1 hour and then transferred into a 50 mL round bottom flask. The reaction was kept at 100° C. for 3 hours in order to further condense RF resins and increase their cross-linking ratios. After cooling down to room temperature, the solution was washed three times by water. Then obtained $Fe_3O_4$/Aus@RF was finally dispersed in 2 mL of water.

Seed-mediated growth of Au nanoshells: In a typical process, 500 μL of PVP (50 mg/mL, Mw=40000), 100 μL of NaOL (10 mM), 20 μL of $HAuCl_4$ (0.25 M) and 50 μL of $H_2O_2$ were added into 7.5 mL of deionized water in sequence. Then, 25 μL of $Fe_3O_4$/Aus@RF solution was added. The reaction occurred at room temperature for 30 min. The product was washed by deionized water three times and dispersed in deionized water for characterization.

Figures 13A, 13B, 13C, 13D, 13E, 13F, 13G:
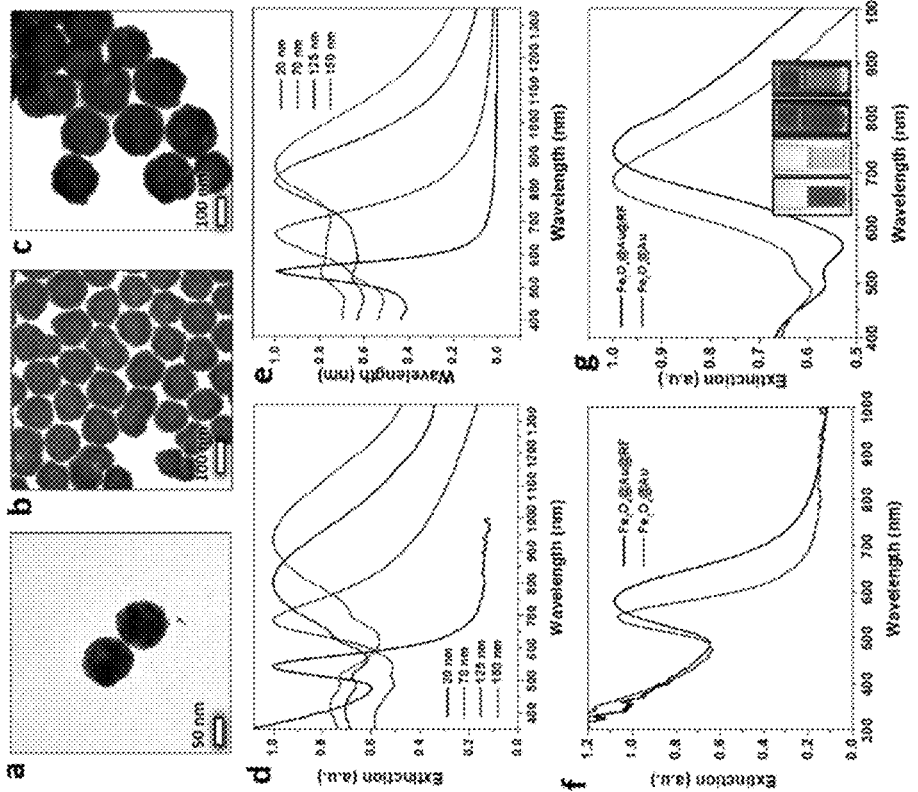
FIGS. 13a-FIG. 13g illustrate TEM images of $Fe_3O_4$@Au nanoparticles prepared by etching away RF shells in NaOH solutions. Core sizes: 20 nm (FIG. 13a), 70 nm (FIG. 13b), and 125 nm (FIG. 13c).

Etching RF shells: The solutions of $Fe_3O_4$@Au@RF nanoparticles were first dispersed in 2 M of NaOH solutions. To improve dispersibility of colloidal particles, the reaction occurred under the presence of 0.5 M PVP. After incubating at 80° C. overnight, $Fe_3O_4$@Au nanoparticles were washed by DI water for three times. The removal of RF also led to a blueshift from 730 nm to 685 nm in the plasmon band of Au shells synthesized with 70-nm cores (FIG. 13g). Against a bright background, the perceived color in the colloidal dispersion was complementary to the plasmonic extinction. Therefore, the color turned from green to light blue (left two panels in the inset of FIG. 13g). Interestingly, against a dark background, both the solutions before and after removing RF shells appeared red (right two panels in FIG. 13g), which is ascribed to their strong scattering of red light between 622 and 770 nm.

Characterization: Extinction spectra were measured by Ocean Optics HR2000 spectrometer. TEM images were taken on Tecnai 12 transmission electron microscope at 120 kV. Dark-field optical macroscopic images were taken using A Zeiss AXIO Imager optical microscope. The SEM images were taken on ThermoFisher Scientific (formerly FEI/Philips) NNS450 scanning electron microscope with a backscattering electron detector. The elemental mapping was performed at 50 kV.

Fabrication of Plasmonic Films

Preparation of PVA-Au composite films: PDMS film served as a transparent substrate for the PVA-plasmonic composite films. Silicone elastomer curing agent and silicone elastomer base were thoroughly mixed with a mass ratio of 1 to 10. The mixture was placed at ambient conditions for 2 hours to remove the air bubble inside the viscous solution. Then, it was cured at 60° C. for two hours. 10% PVA solution was first prepared by dissolving PVA into deionized water under sonication. Then a certain amount of PVA solution was added into the Au shell solution with a final concentration of about 0.005 mg/mL. The obtained mixture solution was spin-casted on a PDMS substrate. To form a uniform thin PVA film, the PDMS substrate was first treated by plasma for 20 min. The casted film was dried in a vacuum at room temperature.

Preparation of anti-counterfeiting films: 2-Hydroxy-2-methylpropiophenone serves as a photoinitiator. AM is monomer and BIS is the cross-linking agent. In a typical process, 250 mg of AM, 14 mg of BIS and 3 μL of 2-Hydroxy-2-methylpropiophenone were added in 1 mL of DEG. Au shell was first precipitated by centrifugation and then dispersed in the DEG solution. The mixture solution was sandwiched between glass slides and then was exposed to UV light (254 nm) for 1 min. A photomask with a pre-designed pattern was placed atop the sample, followed by applying a magnetic field ($B_1$). After the first UV exposure, 1D plasmonic chains with parallel alignment to external fields were fixed in the uncovered areas. The photomask was then removed, and a second UV exposure was applied to polymerize the remaining parts of the film under a horizontal magnetic field ($B_2$). The magnetic alignment was achieved by placing the mixture into the center of two identical permanent magnets. The field strength was measured to be 25 mT (250 G).

Analyzing Optical Properties of Au Nanoshells by Finite Element Method

Calculating optical cross-section of single Au nanoshell: The computation of optical cross-section and efficiency is achieved based on the finite element method (Comsol Multiphysics). A sphere with core-shell-shell geometry is modeled to mimic the $Fe_3O_4$@Au@RF nanostructures. The refractive index of RF is identified as 1.5. The domain of Au is defined by the built-in "Au" materials. Their physical properties, like the wavelength-dependent complex refractive index, have been fully described in the material library of Comsol Multiphysics. For the $Fe_3O_4$ domain, their refractive index is also wavelength-dependent and has a complex value with the real part determining the scattering properties and imaginary part determining the absorption of $Fe_3O_4$ material. To analyze the size-dependent opportunities of Au shell (FIGS. 1a-1f), the thickness of Au and RF shell is 25 nm and 20 nm, respectively. Instead, the diameter of the magnetic core increases from 20 to 30, 50, 70, 80, 90, 100, 125, and 150 nm. Their scattering ($\sigma_{sca}$), absorption ($\sigma_{abs}$) and extinction ($\sigma_{ext}$) cross-sections are calculated by solving the Maxwell equations in Comsol Multiphysics. The optical coefficients (Q) of Au shell, like scattering and absorption coefficient, were calculated by dividing the corresponding optical cross-sections by the physical cross-sections of the Au shell. The correlation between them can be expressed as $\sigma = Q\pi r^2$, where r is the radius of the Au shell.

Analyzing the coupling between Au nanoshells within plasmonic chains: The optical cross-sections of plasmonic chains were also calculated by the finite element method. In geometry, a 1D chain containing Au shells with well-controlled interparticle separation and orientation was first created in the Comsol Multiphysics. Then, the $\sigma_{ext}$ was calculated and normalized to a number of Au shells in the 1D chains.

Preparation of Transparent Display

Figures 18A, 18B, 18C, 18D, 18E, 18F, 18G:
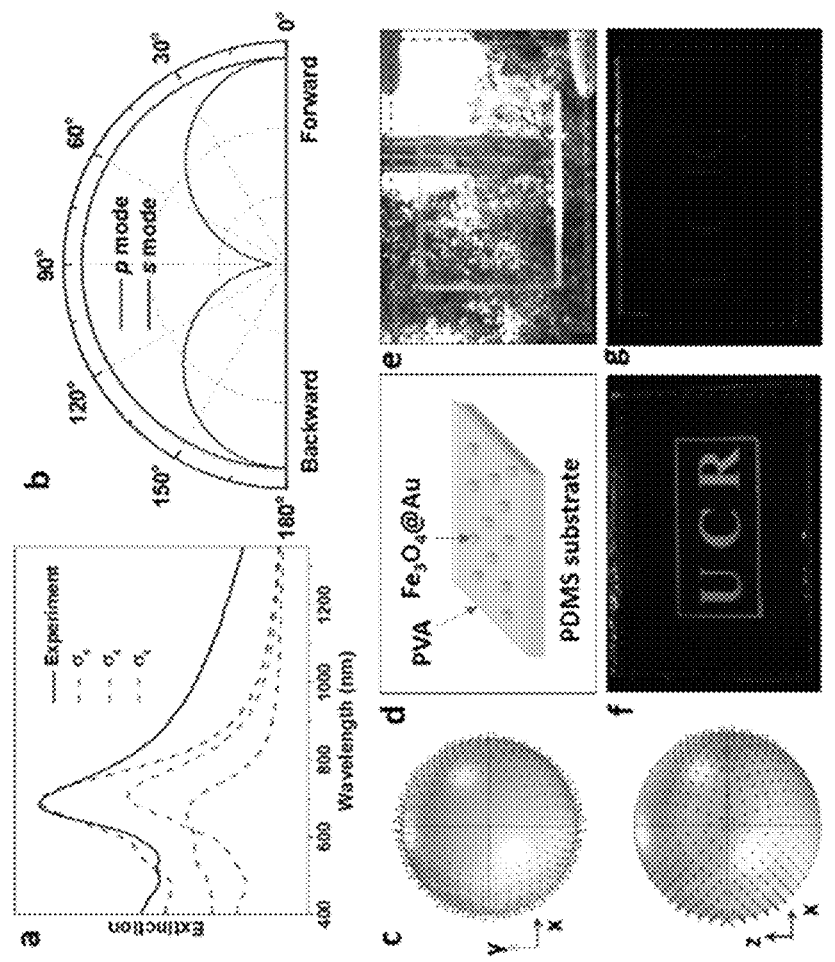
FIG. 18a illustrate optical properties of Au shells prepared by using 70 nm $Fe_3O_4$ nanoparticles as cores.
FIG. 18b is a polar plot showing the angular distribution of scattered light of Au shells at 738 nm under p- and s-mode excitation.
FIG. 18c illustrates the corresponding surface Poynting vector and electric field distribution of Au shells.
FIG. 18d illustrates the fabrication of PVA/Au composite film for transparent displays.
FIG. 18e is a photograph of the fabricated film under natural light. Photographs showing the transparent displays made of FIG. 18f PVA/Au composite film and FIG. 18g of a pure PVA film.

In accordance with an exemplary embodiment, to take advantage of the strong scattering of the Au shells, a transparent display was prepared by incorporating Au shells into PVA films. Their scattering properties were first investigated by finite element analysis. As shown in FIG. 18*a*, the peak position of the measured spectra of $Fe_3O_4$@Au with 70 nm core agrees well with the calculated cross-section. The slight discrepancy at off-resonance wavelength is probably due to the broad-band absorption of iron oxides. The calculated cross-sections confirm that the resonant scattering of Au shells is much stronger than the absorption, thus confirming that Au shells are ideal for transparent displays as they only scatter light at a particular wavelength while maintaining "transparent" elsewhere. Under p-mode (FIG. 18*b*), a similar scattering pattern was observed as the Lambertian distribution of an ideal diffusely reflecting surface. In the case of s-mode, however, the scattering occurred in a broader scope, indicating that the scattering of the Au shell can be viewed from a wide-angle. The Poynting vectors and localized electric field distribution are shown in FIG. 18*c*, which further confirms the wide-angle scattering of Au shells. To incorporate Au shells into a transparent polymer matrix, 10% weight of PVA aqueous solution was added into Au shell dispersion with a final concentration of approximately 0.005 mg/mL. The mixture was spin-casted on a PDMS film and left at the ambient condition to remove bubbles and dry out (FIG. 18*d*). The digital picture of the film shown in FIG. 18*e* indicates the high transparency of the fabricated film as the details of behind landscape could be observed with only slight changes in their appearance color and brightness. In FIG. 18*f*, a transparent film was shown at work with red letters projected on the screen. The projected image showed up clearly and can be viewed from all directions. Conversely, the pure polymer film without Au shell appeared dark and the image can barely be observed under the same laser projector due to the lack of scattering (FIG. 18*g*).

In accordance with an exemplary embodiment, a method of forming magnetic/plasmonic hybrid structures, which includes synthesizing colloidal magnetic nanoparticles; modifying the magnetic nanoparticles in a solution of a polymeric ligand; binding metal seed nanoparticles to the surface of the magnetic nanoparticles; and performing a seed-mediated growth on the metal seed nanoparticles by reducing a metal salt in solution to form the magnetic/plasmonic hybrid structures. The method can further include coating the magnetic nanoparticles containing surface-attached metal seed nanoparticles with a polymer shell of resorcinol-formaldehyde resin prior to performing the seed-mediated growth. In addition, optionally removing the resorcinol-formaldehyde coating from the plasmonic structures after the seed-mediated growth.

In accordance with an exemplary embodiment, the polymeric ligand is polyethyleneimine (PEI). The magnetic nanoparticles comprise iron oxide, for example, $Fe_3O_4$. The metal seed nanoparticles can include gold, silver, or copper. In addition, the metal salt can include salt of gold, silver, or copper.

In accordance with an exemplary embodiment, the method can further include mediating and confining the seeded growth of the metal on the magnetic nanoparticles with the polymeric ligand, the polymeric ligand forming a deformable and permeable polymer shell on the magnetic nanoparticles that suppresses a deposition of metal atoms and limit growth of the metal atoms along a radial direction. In addition, the magnetic/plasmonic hybrid structures can be a plurality of the magnetic/plasmonic hybrid structures, which are magnetically assembled into plasmonic chains in an active transparent display or an anti-counterfeiting device. In accordance with an exemplary embodiment, the synthesizing of the colloidal particles can be controlled to an outer diameter of between 10 nm to 150 nm.

The detailed description above describes versions of a method for forming magnetic/plasmonic hybrid structures, methods for use of magnetic/plasmonic hybrid structures, and magnetic/plasmonic hybrid structures representing examples of the inventive the method for forming magnetic/plasmonic hybrid structures, methods for use of magnetic/plasmonic hybrid structures, and magnetic/plasmonic hybrid structures disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of forming magnetic/plasmonic hybrid structures comprising:
   synthesizing colloidal magnetic nanoparticles;
   modifying the magnetic nanoparticles in a solution of a polymeric ligand;
   binding metal seed nanoparticles to the surface of the magnetic nanoparticles;
   performing a seed-mediated growth on the metal seed nanoparticles by reducing a metal salt in solution to form the magnetic/plasmonic hybrid structures; and
   coating the magnetic nanoparticles containing surface-attached metal seed nanoparticles with a polymer shell of resorcinol-formaldehyde resin prior to performing the seed-mediated growth.

2. The method according to claim 1, further comprising:
   removing the resorcinol-formaldehyde coating from the plasmonic structures after the seed-mediated growth.

3. The method according to claim 1, wherein the polymeric ligand is polyethyleneimine (PEI).

4. The method according to claim 1, wherein the magnetic nanoparticles comprise iron oxide.

5. The method according to claim 4, wherein the iron oxide is $Fe_3O_4$.

6. The method according to claim 1, wherein the metal seed nanoparticles comprises gold, silver, or copper.

7. The method according to claim 1, wherein the metal salt comprises salt of gold, silver, or copper.

8. The method according to claim 1, further comprising:
controlling the synthesizing of the colloidal particles to a width from 10 nm to 150 nm.

9. The method according to claim 1, further comprising:
utilizing the plasmonic structure in a biomedical application.

10. A method of forming magnetic/plasmonic hybrid structures comprising:
synthesizing colloidal magnetic nanoparticles;
modifying the magnetic nanoparticles in a solution of a polymeric ligand;
binding metal seed nanoparticles to the surface of the magnetic nanoparticles;
performing a seed-mediated growth on the metal seed nanoparticles by reducing a metal salt in solution to form the magnetic/plasmonic hybrid structures; and
mediating and confining the seeded growth of the metal on the magnetic nanoparticles with the polymeric ligand, the polymeric ligand forming a deformable and permeable polymer shell on the magnetic nanoparticles that suppresses a deposition of metal atoms and limit growth of the metal atoms along a radial direction.

11. A method of forming magnetic/plasmonic hybrid structures comprising:
synthesizing colloidal magnetic nanoparticles;
modifying the magnetic nanoparticles in a solution of a polymeric ligand;
binding metal seed nanoparticles to the surface of the magnetic nanoparticles;
performing a seed-mediated growth on the metal seed nanoparticles by reducing a metal salt in solution to form the magnetic/plasmonic hybrid structures, and
wherein the magnetic/plasmonic hybrid structures comprises a plurality of the magnetic/plasmonic hybrid structures, further comprises:
magnetically assembling the plurality of the magnetic/plasmonic hybrid structures into plasmonic chains in an active transparent display or an anti-counterfeiting device.

* * * * *